United States Patent [19]

Prisbylla

[11] Patent Number: 4,859,228
[45] Date of Patent: Aug. 22, 1989

[54] NOVEL 5-AMINOMETHYLENE-2,4-IMIDAZOLIDINEDIONES AND 5-AMINOMETHYLENE-2-THIONOIMIDAZOLIDINE-4-ONES

[75] Inventor: Michael P. Prisbylla, Richmond, Calif.

[73] Assignee: ICI Americas Inc, Wilmington, Del.

[21] Appl. No.: 74,216

[22] Filed: Jul. 16, 1987

[51] Int. Cl.⁴ .................... C07D 233/96; A01N 43/50
[52] U.S. Cl. .......................................... 71/92; 71/94; 548/308; 548/309; 548/314; 546/210; 546/278; 540/603
[58] Field of Search ............ 548/308, 309, 314; 546/210, 278; 540/603; 711/92.94

[56] References Cited
U.S. PATENT DOCUMENTS

| | | | |
|---|---|---|---|
| 3,818,032 | 6/1974 | Moser et al. | 548/116 |
| 3,990,883 | 11/1976 | Clapot et al. | 546/278 |
| 4,036,850 | 7/1977 | Enders | 548/314 |
| 4,345,935 | 8/1982 | Thibault | 71/92 |
| 4,345,936 | 8/1982 | Thibault | 71/92 |
| 4,684,735 | 8/1987 | Mirviss | 548/308 |

Primary Examiner—Mary C. Lee
Assistant Examiner—Zinna Northington
Attorney, Agent, or Firm—Harry A. Pacini

[57] ABSTRACT

Compounds of the formula

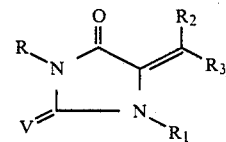

wherein R is alkyl, phenyl, substituted phenyl, alkylsulfonyl, alkoxy, halo or haloalkyl; $R_1$ is hydrogen, alkyl, phenyl, or halo substituted phenyl; $R_2$ is hydrogen or alkyl; $R_3$ is

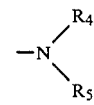

wherein $R_4$ and $R_5$ are independently hydrogen, alkyl, phenyl, halophenyl, phenalkyl, halophenalkyl, cycloalkyl, cycloalkylmethyl, naphthyl, pyridyl, pyridylalkyl, or $R_4$ and $R_5$ taken together with nitrogen form a hexamethyleneimine, piperidine, phenylpiperidine, benzylpiperidine, indoline, phenyl indoline or perhydroindole; and V is oxygen or sulfur; provided that when $R_1$ is methyl and $R_3$ is

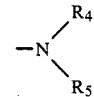

wherein $R_4$ is methyl and $R_5$ is phenyl, then R is other than 2-chlorophenyl or 2-methoxyphenyl; and when $R_1$ is hydrogen or ethyl and $R_3$ is

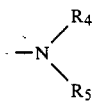

wherein $R_4$ is methyl and $R_5$ is phenyl, then R is other than 3,4-dichlorophenyl; and herbicidal compositions and methods utilizing said compounds.

122 Claims, No Drawings

NOVEL 5-AMINOMETHYLENE-2,4-IMIDAZOLIDINEDIONES AND 5-AMINOMETHYLENE-2-THIONOIMIDAZOLIDINE-4-ONES

FIELD OF THE INVENTION

This invention relates to herbicides and, more particularly to certain novel substituted 5-aminomethylene-2,4-imidazolidinediones and 5-aminomethylene-2-thionoimidazolidine-4-ones which are useful as herbicides.

DESCRIPTION OF THE INVENTION

This invention relates to novel herbicidal compounds having the formula

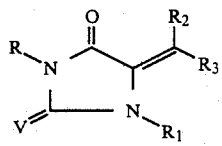

wherein R and $R_1$ are independently selected from the group consisting of alkyl, phenyl and phenyl substituted with alkyl, alkylsulfonyl, alkoxy, halo, haloalkyl, or combinations thereof;
$R_2$ is hydrogen or alkyl;
$R_3$ is

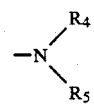

wherein $R_4$ and $R_5$ are independently hydrogen, alkyl, phenyl, halophenyl, phenalkyl, halophenalkyl, cycloalkyl, cycloalkylmethyl, naphthyl, pyridyl, pyridylalkyl, combinations thereof, or $R_4$ and $R_5$ taken together with N form a ring such as, but not limited to, indoline, piperidine, phenylpiperidine, phenalkylpiperidine, perhydroindole, or hexamethyleneimine; and V is oxygen or sulfur; provided that when $R_1$ is methyl and $R_3$ is

wherein $R_4$ is methyl and $R_5$ is phenyl, then R is not 2-chlorophenyl or 2-methoxyphenyl; and when $R_1$ is hydrogen or ethyl and $R_3$ is

wherein $R_4$ is methyl and $R_5$ is phenyl, then R is not 3,4-dichlorophenyl.

The term "cycloalkyl" includes saturated cyclic hydrocarbyl moieties and includes such moieties having from 3 to 6 carbon atoms. The term "alkyl" includes both straight and branched chain saturated acyclic hydrocarbyl moieties and includes such moieties having from 1 to 6 carbon atoms such as methyl, ethyl, n-propyl, isopropyl, n-butyl, sec-butyl, isobutyl and tertbutyl, as well as the 6 pentyls and 16 hexyls. Where the alkyl group is used to connect moieties such as phenyl, halogen, sulfonyl or pyridyl, the term "alkyl" includes such hydrocarbyl moieties having from 1–3 carbon atoms such as methyl, ethyl and propyl. The term "alkoxy" includes both straight and branched saturated acyclic hydrocarbyl moieties which contain an oxygen in the chain and includes such moieties having from 1 to 4 carbon atoms, for example methoxy, ethoxy, n-propoxy, isopropoxy, n-butoxy, sec-butoxy, isobutoxy and t-butoxy. The term "halo" includes fluorine, chlorine, bromine or iodine as mono, di, tri and mixed halogen substitutions.

The compounds of this invention have been found to be active herbicides in possessing herbicidal activity against various species of weeds. In the broadest sense, the term "weeds" refers to plants which grow in locations in which they are not desired.

This invention also therefore relates to a method for controlling undesirable vegetation, comprising applying to a locus where control of such vegetation is desired an herbicidally effective amount of a compound as described herein, and also relates to herbicidal compositions of matter comprising an herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

The compounds of this invention may be prepared as shown in the following schematic, by reacting the imidazolidine-2,4-dione or 2-thionoimidazolidine-4-one of choice with the amine of choice and an orthoformate which includes, but is not limited to, trimethyl or triethylorthoformate. This reaction generally proceeds in the presence of a solvent, with or without a catalyst, at an elevated temperature and standard pressure.

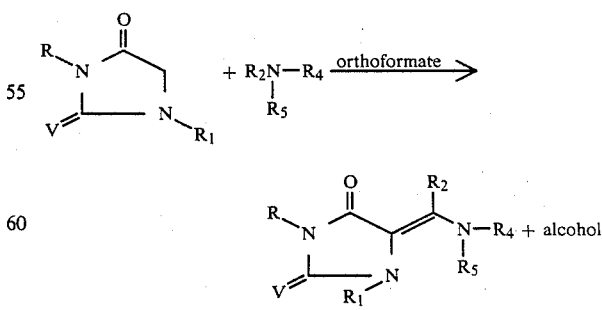

The solvent of this reaction can be either an excess of the amine reactant or an aliphatic hydrocarbon, aromatic hydrocarbon, halogenated hydrocarbon or ether; preferably the solvent is an aromatic hydrocarbon.

The catalysts which can be used include sulfonic acids such as p-toluene sulfonic acid, benzoic acids, carboxylic acids such as trichloroacetic acid, mineral acids such as HCl and Lewis acids such as boron trifluoride etherate; preferably the catalyst is a sulfonic acid such as p-toluene sulfonic acid. Catalysts are used in amounts ranging from about 1% to about 10%, preferably about 3%.

The reaction can proceed at temperatures from about 40° C. to about 180° C., preferably from about 60° to about 130° C., most preferably from about 80° to about 115° C., at pressures from about 0.5 to about 2.0 atmospheres, preferably at atmospheric pressure. The products of this reaction can be recovered by standard methods such as concentration under reduced pressure.

The following are examples of the preparation of compounds of this invention, the structures of which were confirmed by infrared, nuclear magnetic resonance and mass spectroscopy.

EXAMPLE 1

Preparation of 5-(N-Ethyl-N-cyclohexylaminomethylene)-3-(2-fluorophenyl)-1-methylimidazolidine-2,4-dione (Compound 71 herein)

In a flask were placed 2.5 grams (g) (0.012 mole) 3-(2-fluorophenyl)-1-methylimidazolidine-2,4-dione, 1.53 g (0.012 mole) N-ethyl-N cyclohexylamine, 12 milliliters (ml) triethylorthoformate, 6 ml toluene and 0.075 g p-toluenesulfonic acid. The contents of the flask were heated while stirring and ethanol was removed via azeotropic distillation. The reaction was continued, adding solvents (triethylorthoformate/toluene, 2:1) as necessary until thin layer chromatography indicated complete consumption of the starting dione. The resulting mixture was concentrated under reduced pressure and purified by column chromatography (silica gel, hexane/ethyl acetate gradient elution) to yield 2.05 g of a solid, melting point 40°–55° C. which was confirmed by infrared, nuclear magnetic resonance and mass spectroscopy to be a mixture of E and Z isomers.

EXAMPLE 2

Preparation of 5-(N-Methyl-N-phenethylaminomethylene)-3-(2,5-difluorophenyl)-1-methylimidazolidine-2,4-dione (Compound 62 herein)

3-(2,5-difluorophenyl)-1-methylimidazolidine-2,4-dione (1.8 g, 8.0 mmole) and N-methyl-N-phenethylamine (1.28 g, 9.5 mmole) were heated to reflux in triethylorthoformate (10 ml) and toluene (5 ml) containing a catalytic amount of p-toluenesulfonic acid (50 mg). Solvent was removed azeotropically until thin layer chromatographic analysis indicated complete consumption of the dione. The mixture was cooled, concentrated and purified by column chromatography (silica gel, hexane/ethyl acetate gradient elution) to afford 2.4 g of a solid as a mixture of E and Z isomers, m.p. 95°–113° C.

EXAMPLE 3

Preparation of 5-(N-Methyl-N-phenylaminomethylene)-3-(3-chlorophenyl)1-methylimidazolidine-2,4-dione (Compound 2 herein)

3-(3-chlorophenyl)-1-methylimidazolidine-2,4-dione (2.25 g, 10 mmole) and N-methyl-N-phenylamine (1.6 g, 15 mmole) were heated to reflux in triethylorthoformate (15 ml) and toluene (15 ml). Solvent volume was reduced to approximately 5 ml via distillation and the solution allowed to cool. Trituration with ether afforded 0.75 g of a yellow solid, m.p. 144°–150° C.

EXAMPLE 4

Preparation of 5-(N-Methyl-N-phenylethylaminomethylene)-3-(2-fluorophenyl)-1-methyl-2-thionoimidazolidine-4-one (Compound 132 herein)

3-(2-Fluorophenyl)-1-methylimidazolidine-2-thiono-4-one (2.2 g, 15 mmole) and N-methyl-N-phenethylamine (2.2 g, 16.5 mmole) were heated at reflux in triethylorthoformate (15 ml) and toluene (8 ml). Solvent volume was reduced by approximately 7.5 ml via distillation and the solution allowed to cool and the solvents removed under reduced pressure. The resulting dark solids were triturated with ethyl acetate to yield 3.2 g of yellow solids. The filtrate was passed through silica and another 2.6 g of crystalline product was collected and combined with the first solids to yield 5.8 g with a melting point of 166°–167° C.

The following Table I illustrates embodiments of this invention. Structures of the indicated compounds were confirmed by spectral analyses.

TABLE I

| Cmpd. No. | R | $R_1$ | $R_2$ | $R_3$ | V | m.p. °C. or nD30 |
|---|---|---|---|---|---|---|
| 1 | Cl-phenyl-Cl | —CH$_3$ | —H | 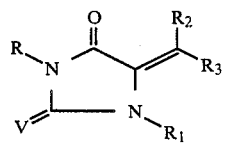 | O | 177–181 |

TABLE I-continued

[Structure: R-N(R)-C(=V)-... with substituents R, R₁, R₂, R₃, V as shown]

| Cmpd. No. | R | R₁ | R₂ | R₃ | V | m.p. °C. or nD30 |
|---|---|---|---|---|---|---|
| 2 | 3-Cl-phenyl | —CH₃ | —H | —N(CH₃)(phenyl) | O | 144–150 |
| 3 | 2-F-phenyl | —CH₃ | —H | —N(CH₃)(phenyl) | O | 52–57 |
| 4 | 3,4-diCl-phenyl | —CH₃ | —H | —N(CH₃)(CH₂-phenyl) | O | oil |
| 5 | 2-F-phenyl | —CH₃ | —H | —N(CH₃)(CH₂-phenyl) | O | 133–135 |
| 6 | phenyl | —CH₃ | —H | —N(CH₃)(phenyl) | O | 48–52 |
| 7 | 3-Cl-phenyl | —CH₃ | —H | —N(CH₃)(CH₂-phenyl) | O | oil |
| 8 | phenyl | —CH₃ | —H | —N(CH₃)(CH₂-phenyl) | O | 119–126 |
| 9 | 2-F-phenyl | —C₂H₅ | —H | —N(CH₃)(phenyl) | O | semi-solid |
| 10 | 3-Cl-phenyl | —C₂H₅ | —H | —N(CH₃)(phenyl) | O | 99–103 |
| 11 | 3-Cl-phenyl | —C₂H₅ | —H | —N(CH₃)(phenyl) | O | 62–70 |

TABLE I-continued

[Structure: R-N(−)−C(=O)−C(=C(R2)(R3))−N(R1)−C(V)= (ring)]

| Cmpd. No. | R | $R_1$ | $R_2$ | $R_3$ | V | m.p. °C. or nD30 |
|---|---|---|---|---|---|---|
| 12 | 3-CF$_3$-phenyl | −CH$_3$ | −H | −N(CH$_3$)−phenyl | O | 64–94 |
| 13 | 3-CH$_3$O-phenyl | −CH$_3$ | −H | −N(CH$_3$)−phenyl | O | oil |
| 14 | 3-CH$_3$-phenyl | −CH$_3$ | −H | −N(CH$_3$)−phenyl | O | oil |
| 15 | 3-CH$_3$-phenyl | −C$_2$H$_5$ | −H | −N(CH$_3$)−phenyl | O | oil |
| 16 | 2-F-phenyl | −CH$_3$ | −H | −N(CH$_3$)−(2-pyridyl) | O | 42–60 |
| 17 | 3-Cl-4-F-phenyl | −CH$_3$ | −H | −N(CH$_3$)−phenyl | O | 167–190 |
| 18 | 3-Cl-4-F-phenyl | −CH$_3$ | −H | −N(CH$_3$)−CH$_2$−phenyl | O | 1.6295 |
| 19 | 3,4-Cl$_2$-phenyl | −CH$_3$ | −H | −N(CH$_3$)−CH$_2$−(2-Cl-phenyl) | O | oil |
| 20 | 3,4-Cl$_2$-phenyl | −CH$_3$ | −H | −N(CH$_3$)−CH$_2$−(4-Cl-phenyl) | O | 1.6232 |

TABLE I-continued

Structure: R-N(R)-C(=O)-C(=N-R₁)(... where the core shows an N=V, with substituents R₂, R₃ on the vinyl position.

| Cmpd. No. | R | R₁ | R₂ | R₃ | V | m.p. °C. or nD30 |
|---|---|---|---|---|---|---|
| 21 | 2-F-phenyl | —CH₃ | —H | —N(CH₃)—CH₂CH₂—phenyl | O | semi-solid |
| 22 | 3,4-diCl-phenyl | —CH₃ | —H | —N(CH₃)—CH₂CH₂—phenyl | O | 1.6386 |
| 23 | phenyl | —CH₃ | —H | —N(CH₃)—CH₂CH₂—phenyl | O | 1.6377 |
| 24 | 3-Cl-phenyl | —CH₃ | —H | —N(CH₃)—CH₂CH₂—phenyl | O | semi-solid |
| 25 | 2-F-phenyl | —CH₃ | —H | —N(CH₃)—cyclohexyl | O | semi-solid isomer #1 |
| 26 | 2-F-phenyl | —CH₃ | —H | —N(CH₃)—cyclohexyl | O | semi-solid isomer #2 |
| 27 | 3,4-diCl-phenyl | —CH₃ | —H | —N(CH₃)—cyclohexyl | O | 42–56 |
| 28 | phenyl | —CH₃ | —H | —N(CH₃)—cyclohexyl | O | 68–79 |
| 29 | 3-Cl-phenyl | —CH₃ | —H | —N(CH₃)—cyclohexyl | O | semi-solid |
| 30 | 4-Cl-phenyl | —CH₃ | —H | —N(CH₃)—phenyl | O | 145–151 |

TABLE I-continued

| Cmpd. No. | R | $R_1$ | $R_2$ | $R_3$ | V | m.p. °C. or nD30 |
|---|---|---|---|---|---|---|
| 31 | 4-Cl-C6H4- | —CH3 | —H | —N(CH3)CH2-C6H5 | O | 1.6392 |
| 32 | 3-Cl-4-F-5-OCH3-C6H2- | —CH3 | —H | —N(CH3)CH2-C6H5 | O | oil |
| 33 | C6H5- | —CH3 | —H | —N(CH3)CH2CH2-(2-pyridyl) | O | 83–101 |
| 34 | 3,4-Cl2-C6H3- | —CH3 | —H | —N(CH3)CH2CH2-(2-pyridyl) | O | 97–102 |
| 35 | 2-F-C6H4- | —CH3 | —H | —N(CH3)CH2CH2-(2-pyridyl) | O | 95–105 |
| 36 | 3-Cl-C6H4- | —CH3 | —H | —N(C6H5)CH2-C6H5 | O | 66–78 |
| 37 | 3-CF3-C6H4- | —CH3 | —H | —N(CH3)CH2-C6H5 | O | oil |
| 38 | 3-CF3-C6H4- | —CH3 | —H | —N(CH3)CH2-(2-Cl-C6H4) | O | semi-solid |
| 39 | 3-CF3-C6H4- | —CH3 | —H | —N(CH3)CH2-(3-Cl-C6H4) | O | 1.6258 |

TABLE I-continued $$\underset{V}{\overset{R}{\underset{|}{N}}}\underset{|}{\overset{O}{\underset{N}{\parallel}}}\underset{R_1}{\overset{R_2}{\underset{|}{C}=C}}\overset{R_2}{\underset{R_3}{}}$$

| Cmpd. No. | R | $R_1$ | $R_2$ | $R_3$ | V | m.p. °C. or nD30 |
|---|---|---|---|---|---|---|
| 40 | 3,4-dichlorophenyl | —CH₃ | —H | 2-chloroanilino (NH) | O | 184–194 |
| 41 | 3-CF₃-phenyl | —CH₃ | —H | N(CH₃)-(4-Cl-phenyl) | O | 90–106 |
| 42 | 2-F-phenyl | —CH₃ | —H | N(CH₃)-(4-Cl-phenyl) | O | 84–124 |
| 43 | 3,4-dichlorophenyl | —CH₃ | —H | N(CH₃)-(4-Cl-phenyl) | O | 210–212 |
| 44 | 3-CF₃-phenyl | —CH₃ | —H | N(CH₃)-CH₂CH₂-phenyl | O | 1.6176 |
| 45 | 2-F-phenyl | —CH₃ | —H | N(C₂H₅)-CH₂-phenyl | O | 108–122 |
| 46 | 2-F-phenyl | —CH₃ | —H | N(CH(CH₃)₂)-phenyl | O | 158–165 |
| 47 | 2-F-phenyl | —CH₃ | —H | N(CH(CH₃)₂)-phenyl | O | 85–95 |
| 48 | 2-F-phenyl | —CH₃ | —H | N(CH(CH₃)₂)-CH₂-phenyl | O | 40–53 |

TABLE I-continued

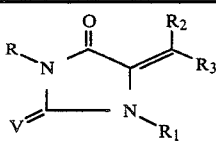

| Cmpd. No. | R | $R_1$ | $R_2$ | $R_3$ | V | m.p. °C. or nD30 |
|---|---|---|---|---|---|---|
| 49 | 2,4-difluorophenyl | —CH$_3$ | —H | —N(CH$_3$)(phenyl) | O | 56–69 |
| 50 | 2,4-difluorophenyl | —CH$_3$ | —H | —N(CH$_3$)(CH$_2$-phenyl) | O | 128–129 |
| 51 | 3-fluoro-4-methylphenyl | —CH$_3$ | —H | —N(CH$_3$)(phenyl) | O | 140–142 |
| 52 | 3-fluoro-4-methylphenyl | —CH$_3$ | —H | —N(CH$_3$)(CH$_2$-phenyl) | O | oil |
| 53 | phenyl | —CH$_3$ | —H | —NH-(2,3-dichlorophenyl) | O | 172–190 |
| 54 | 3-chlorophenyl | —CH$_3$ | —H | —N(CH$_2$-phenyl)$_2$ | O | 35–45 |
| 55 | 2-fluorophenyl | —CH$_3$ | —H | —N(CH$_2$CH$_2$CH$_3$)(CH$_2$-cyclopropyl) | O | oil |
| 56 | 3-trifluoromethyl-4-fluorophenyl | —CH$_3$ | —H | —N(CH$_3$)(phenyl) | O | 151–153 |
| 57 | 3-trifluoromethyl-4-fluorophenyl | —CH$_3$ | —H | —N(CH$_3$)(CH$_2$-phenyl) | O | 70–81 |

TABLE I-continued
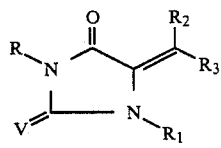
| Cmpd. No. | R | R₁ | R₂ | R₃ | V | m.p. °C. or nD30 |
|---|---|---|---|---|---|---|
| 58 | 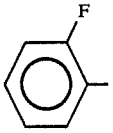 | —CH₃ | —H | 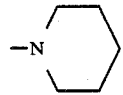 | O | 144–146 |
| 59 | 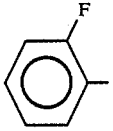 | —CH₃ | —H | 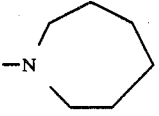 | O | 106–116 |
| 60 | 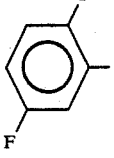 | —CH₃ | —H | 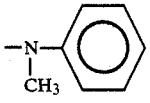 | O | 80–117 |
| 61 | 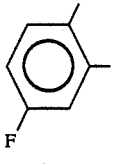 | —CH₃ | —H | 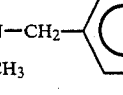 | O | 155–158 |
| 62 | 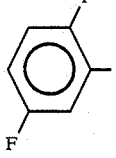 | —CH₃ | —H | 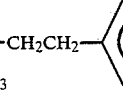 | O | 95–113 |
| 63 | 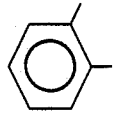 | —CH₃ | —H | $-N\begin{matrix}CH_2CH_2CH_3\\CH_2CH_2CH_3\end{matrix}$ | O | oil |
| 64 | 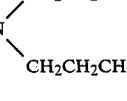 | —CH₃ | —H | 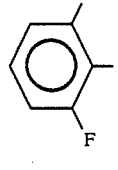 | O | 113–129 |
| 65 | 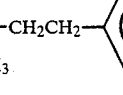 | —CH₃ | —H | 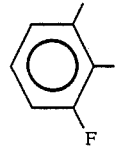 | O | 102–115 |

TABLE I-continued

Structure:

$$\text{R-N(H?)-C(=O)-C(R_2)=C(R_3)... N-R_1, with V}$$

| Cmpd. No. | R | $R_1$ | $R_2$ | $R_3$ | V | m.p. °C. or nD30 |
|---|---|---|---|---|---|---|
| 66 | 3-Cl-4-CH₃-phenyl | —CH₃ | —H | —N(CH₃)—CH₂CH₂—phenyl | O | semi-solid |
| 67 | 3-F-4-CH₃-phenyl | —CH₃ | —H | —N(CH₃)—CH₂CH₂—phenyl | O | 96–101 |
| 68 | 3-CF₃-4-F-phenyl | —CH₃ | —H | —N(CH₃)—CH₂CH₂—phenyl | O | 124–132 |
| 69 | 3-Cl-4-CH₃-phenyl | —CH₃ | —H | —N(CH₃)—CH₂—phenyl | O | 128–135 |
| 70 | 3-Cl-4-CH₃-phenyl | —CH₃ | —H | —N(CH₃)—phenyl | O | 166–169 |
| 71 | 2-F-phenyl | —CH₃ | —H | —N(C₂H₅)—phenyl | O | 40–55 |
| 72 | 4-CH₃-phenyl | —CH₃ | —H | —N(CH₃)—CH₂CH₂—phenyl | O | 124–126 |
| 73 | 4-CH₃O-phenyl | —CH₃ | —H | —N(CH₃)—CH₂CH₂—phenyl | O | 102–106 |
| 74 | 4-CH₃-phenyl | —CH₃— | —H | —N(CH₃)—CH₂—phenyl | O | 113–116 |
| 75 | 4-CH₃O-phenyl | —CH₃ | —H | —N(CH₃)—CH₂—phenyl | O | 89–97 |

TABLE I-continued
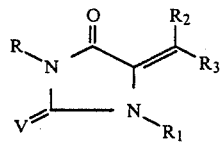
| Cmpd. No. | R | R₁ | R₂ | R₃ | V | m.p. °C. or nD30 |
|---|---|---|---|---|---|---|
| 76 | 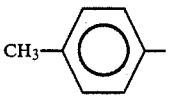 | —CH₃ | —H | 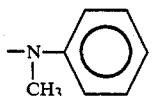 | O | 128–131 |
| 77 | 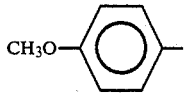 | —CH₃ | —H | 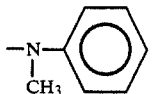 | O | 112–117 |
| 78 | 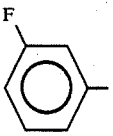 | —CH₃ | —H | 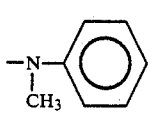 | O | 114–116 |
| 79 | 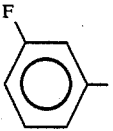 | —CH₃ | —H | 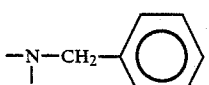 | O | 67–80 |
| 80 | 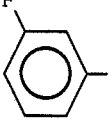 | —CH₃ | —H | 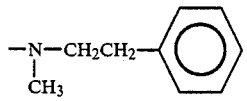 | O | 83–87 |
| 81 | 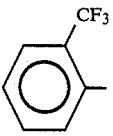 | —CH₃ | —H | 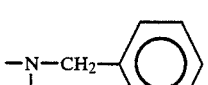 | O | 168–172 |
| 82 | 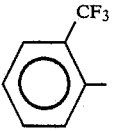 | —CH₃ | —H | 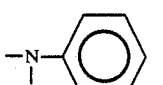 | O | 168–170 |
| 83 | 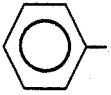 | —CH₃ | —H | 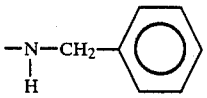 | O | 171–175 |
| 84 | 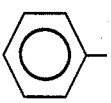 | —CH₃ | —H | 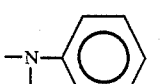 | O | 105–133 |
| 85 | 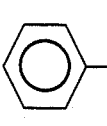 | —CH₃ | —H | 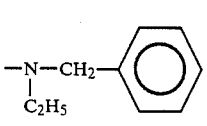 | O | semi-solid |

TABLE I-continued
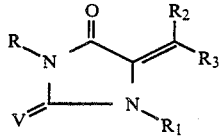
| Cmpd. No. | R | $R_1$ | $R_2$ | $R_3$ | V | m.p. °C. or nD30 |
|---|---|---|---|---|---|---|
| 86 | 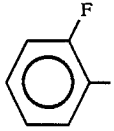 | —CH₃ | —CH₃ | 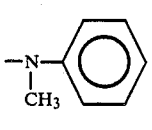 | O | oil |
| 87 | 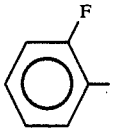 | —CH₃ | —H | 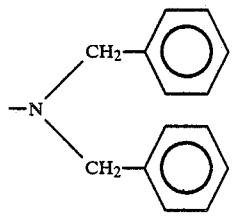 | O | 53–60 |
| 88 | 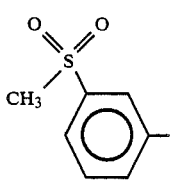 | —CH₃ | —H | 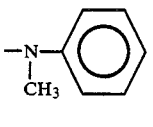 | O | 80–148 |
| 89 |  | —CH₃ | —H | 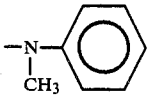 | O | 159–161 |
| 90 | 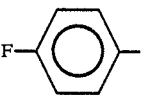 | —CH₃ | —H | 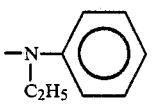 | O | 101–115 |
| 91 | 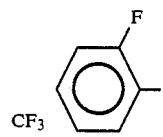 | —CH₃ | —H | 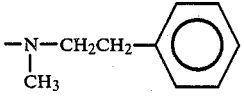 | O | semi-solid |
| 92 | 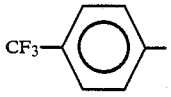 | —CH₃ | —H | 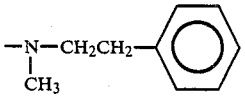 | O | 111–114 |
| 93 | 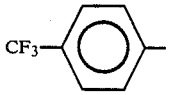 | —CH₃ | —H | 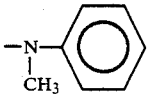 | O | 196–198 |
| 94 | 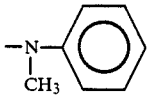 | —CH₃ | —H | 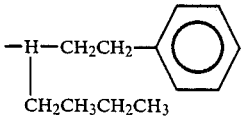 | O | oil |

TABLE I-continued
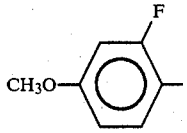
| Cmpd. No. | R | $R_1$ | $R_2$ | $R_3$ | V | m.p. °C. or nD30 |
|---|---|---|---|---|---|---|
| 95 | 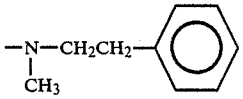 | —CH₃ | —H | 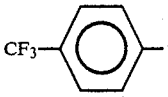 | O | 89–109 |
| 96 | 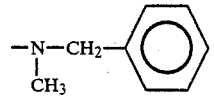 | —CH₃ | —H | 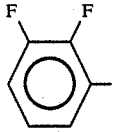 | O | semi-solid |
| 97 | 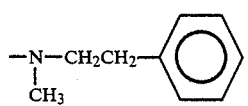 | —CH₃ | —H | 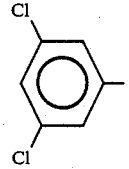 | O | oil |
| 98 | 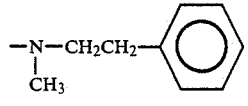 | —CH₃ | —H | 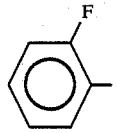 | O | oil |
| 99 | 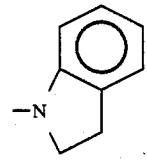 | —CH₃ | —H | 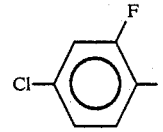 | | 166–169 |
| 100 | 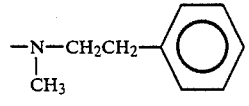 | —CH₃ | —H | 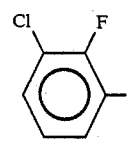 | O | 79–91 |
| 101 | 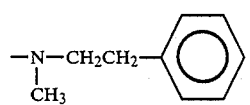 | —CH₃ | —H | 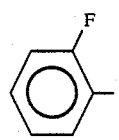 | O | 48–53 |
| 102 | 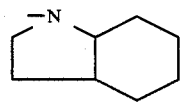 | —CH₃ | —H | 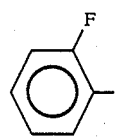 | | 53–60 |
| 103 | 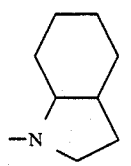 | —CH₃ | —H | | O | oil |

TABLE I-continued
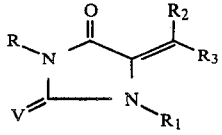
| Cmpd. No. | R | R₁ | R₂ | R₃ | V | m.p. °C. or nD30 |
|---|---|---|---|---|---|---|
| 104 | 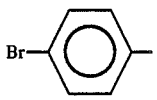 4-Br-phenyl | —CH₃ | —H | 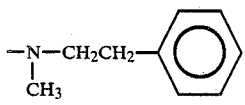 —N(CH₃)CH₂CH₂-phenyl | O | 123–132 |
| 105 | 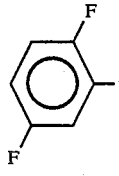 2,4-diF-phenyl | —CH₃ | —H | 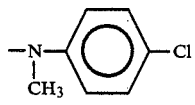 —N(CH₃)-(4-Cl-phenyl) | O | 176–178 |
| 106 | 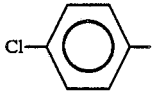 4-Cl-phenyl | —CH₃ | —H | 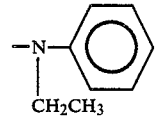 —N(CH₂CH₃)-phenyl | O | 87–105 |
| 107 | 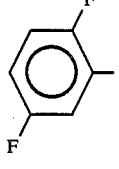 2,4-diF-phenyl | —CH₃ | —H | 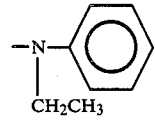 —N(CH₂CH₃)-phenyl | O | 135–141 |
| 108 | 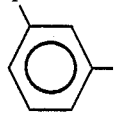 3-I-phenyl | —CH₃ | —H | 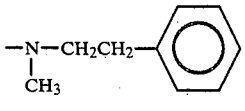 —N(CH₃)CH₂CH₂-phenyl | O | oil |
| 109 | 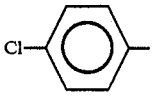 4-Cl-phenyl | —CH₃ | —H | 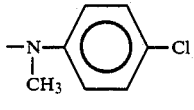 —N(CH₃)-(4-Cl-phenyl) | O | 190–192 |
| 110 | 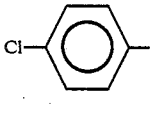 4-Cl-phenyl | —CH₃ | —H | 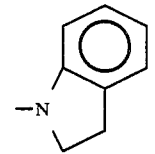 indolinyl | O | 219–221 |
| 111 | 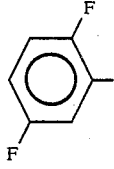 2,4-diF-phenyl | —CH₃ | —H | 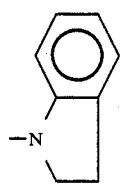 indolinyl | O | 164–166 |

TABLE I-continued
| Cmpd. No. | R | $R_1$ | $R_2$ | $R_3$ | V | m.p. °C. or nD30 |
|---|---|---|---|---|---|---|
| 112 | 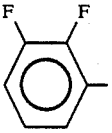 | —CH₃ | —H | 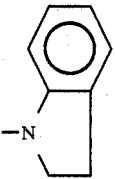 | O | 169–170 |
| 113 | 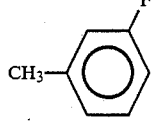 | —CH₃ | —H | 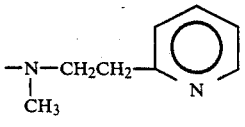 | O | 72–94 |
| 114 | 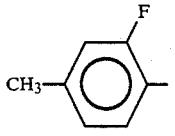 | —CH₃ | —H | 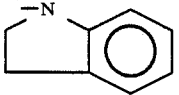 | | 194–195 |
| 115 | 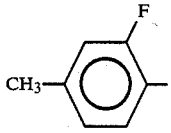 | —CH₃ | —H | 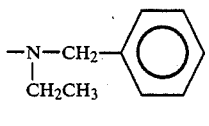 | O | oil |
| 116 | 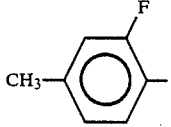 | —CH₃ | —H | 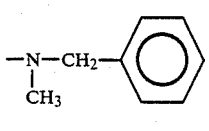 | O | 48–60 |
| 117 | 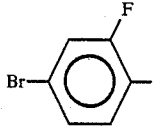 | —CH₃ | —H | 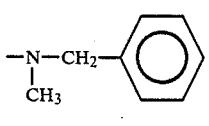 | O | 98–118 |
| 118 | 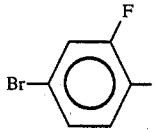 | —CH₃ | —H | 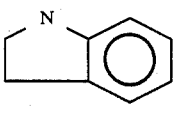 | O | 222–223 |
| 119 | 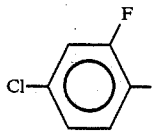 | —CH₃ | —H | 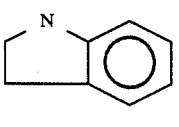 | O | 216–217 |
| 120 | 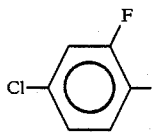 | —CH₃ | —H | 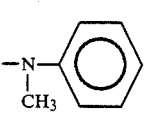 | O | 157–158 |

TABLE I-continued $$\underset{R_1}{\overset{R}{\underset{V}{\text{N}}}}\overset{O}{\underset{}{\text{C}}}\overset{R_2}{\underset{R_3}{\text{C}=}}$$

| Cmpd. No. | R | R₁ | R₂ | R₃ | V | m.p. °C. or nD30 |
|---|---|---|---|---|---|---|
| 121 | 4-Br-3-F-phenyl | —CH₃ | —H | —N(CH₃)(phenyl) | O | 168–171 |
| 122 | 2,3-difluorophenyl | —CH₃ | —H | —N(CH₃)(phenyl) | O | 56–70 |
| 123 | phenyl | —CH₃ | —H | indolin-1-yl | | 154–161 |
| 124 | 3-F-4-CH₃-phenyl | —CH₃ | —H | —N(CH₂CH₃)(phenyl) | O | 58–66 |
| 125 | 2-F-phenyl | —CH₃ | —H | 4-phenylpiperidin-1-yl | O | 64–72 |
| 126 | 2-F-phenyl | —CH₃ | —H | 4-benzylpiperidin-1-yl | O | 54–63 |
| 127 | 2-F-phenyl | —CH₃ | —H | N-ethyl-N-(1-naphthyl) | O | 68–80 |
| 128 | 2-F-phenyl | —CH₃ | —H | —N(CH₃)(CH₂CH₂CH₂-phenyl) | O | oil |
| 129 | phenyl | —CH₃ | —H | —N(CH₃)(phenyl) | S | semi-solid |

TABLE I-continued $$\underset{V}{\overset{R}{\underset{N}{\bigvee}}}\overset{O}{\underset{N}{\bigvee}}\overset{R_2}{\underset{R_1}{\bigvee}}R_3$$

| Cmpd. No. | R | R₁ | R₂ | R₃ | V | m.p. °C. or nD30 |
|---|---|---|---|---|---|---|
| 130 | 3,4-diCl-C₆H₃- | —CH₃ | —H | —N(CH₃)—CH₂—C₆H₅ | S | 46-59 |
| 131 | C₆H₅- | —CH₃ | —H | —N(CH₃)—CH₂—C₆H₅ | S | 133-142 |
| 132 | 2-F-C₆H₄- | —CH₃ | —H | —N(CH₃)—CH₂CH₂—C₆H₅ | S | 166-167 |
| 133 | —CH₃ | 2-F-C₆H₄- | —H | —N(CH₃)—CH₂CH₂—C₆H₅ | O | oil |
| 134 | —CH₃ | 2,5-diF-C₆H₃- | —H | —N(CH₃)—CH₂CH₂—C₆H₅ | O | oil |
| 135 | —CH₃ | 2-F-C₆H₄- | —H | —N(CH₃)—C₆H₅ | O | 50-60 |
| 136 | —CH₃ | 2-F-C₆H₄- | —H | —N(CH₃)₂ | O | 116-136 |
| 137 | —CH₃ | 2,5-diF-C₆H₃- | —H | —N(CH₃)₂ | O | 146-149 |
| 138 | —CH₃ | 2,5-diF-C₆H₃- | —H | —N(CH₃)₂ | O | 119-121 |

TABLE I-continued

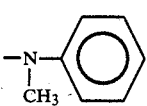

| Cmpd. No. | R | $R_1$ | $R_2$ | $R_3$ | V | m.p. °C. or nD30 |
|---|---|---|---|---|---|---|
| 139 | —CH$_3$ | 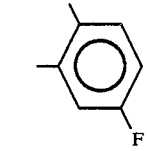 | —H | 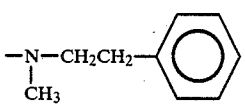 | O | 53–64 |
| 140 | —CH$_3$ | 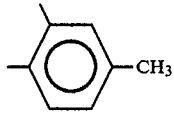 | —H | 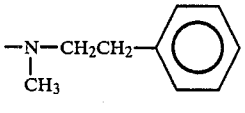 | O | oil |
| 141 | | —CH$_3$ | —H | | O | 132–142 |
| 142 | | —CH$_3$ | —H | 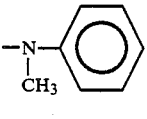 | O | 55–70 |

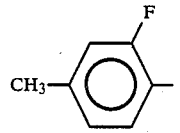

The compounds listed in the foregoing Table I were tested for herbicidal activity by various methods and at various rates of application. Some were tested by more than one method or at more than one rate, but at least one method is shown for each compound to exhibit utility. The following examples are for illustrative purposes only and are not intended as necessarily representative of the overall testing performed. As one skilled in the art is aware, in herbicidal testing a significant number of factors that are not readily controllable can affect the results of individual tests. For example, the results may vary depending on environmental factors, such as amount of sunlight and water, soil type, pH of the soil, temperature, and humidity, among other factors. Also, the depth of planting and the application rate of the herbicide, as well as the nature of crops being tested, can affect the results of the test. Results may vary from crop to crop and within the crop varieties. The methods and activity are as follows:

Pre-Emergence Herbicide Screening Test

Flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were: foxtail (Setaria spp.), watergrass (*Echinochloa crusgalli*), wild oat (*Avena fatua*) and prickly sida (*Sida spinosa*). Broadleaf weeds utilized were annual morningglory (*Ipomoea purpurea*), velvet- leaf (*Abutilon theophrasti*), mustard (*Brassica juncea*), and curly dock (*Rumex crispus*).

One day after planting, the flats were sprayed with a solution of a test compound at a rate of 80 gallons of solution per acre with the compound being applied at a rate of 4 pounds per acre (4.48 kg/ha).

The solutions of the test compounds were made by weighing out 333 mg of the test compound into a 60 ml wide-mouth bottle, dissolving it in 25 ml of acetone containing 1% Tween ® 20 (polyoxyethylene sorbitan monolaurate emulsifier). Additional solvents, not exceeding 5 ml, were used if needed to dissolve the compound. A 20.5 ml aliquot was taken from the stock solution and diluted with 25 ml of an acetone:water mixture (19:1) containing 1% Tween ® 20. This was used as the spray solution.

The flats were returned to the greenhouse after spraying and watered daily by sprinkling. The degree of weed control was estimated and recorded 3 weeks after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; (—) indicates the compound was not tested.

Post-Emergence Herbicidal Evaluation

The soil was prepared and seeded with the same varieties as described for the pre-emergence test. The flats were placed in the greenhouse at 70°–85° F. and watered by sprinkling. Twelve to fourteen days after planting, the flats were sprayed at a rate of 80 gallons of solution per acre. The compound was applied at the rate of 4 pounds/acre (4.48 kg/ha). The spray solution was made up similarly to that described for the pre-emergence evaluation.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, four broadleaf weeds, and yellow nutsedge, respectively, in both pre- and post-emergence evaluations.

TABLE II

| Compound Number | Pre-Emergence control | | | Post-Emergence Control | | |
|---|---|---|---|---|---|---|
| | grasses | broadleaf weeds | nutsedge | grasses | broadleaf weeds | nutsedge |
| 1 | 0 | 0 | 0 | 67 | 80 | 0 |
| 2 | 87 | 85 | 0 | 93 | 93 | 0 |
| 3 | 87 | 95 | 0 | 100 | 98 | 0 |
| 4 | 73 | 81 | 0 | 66 | 100 | 0 |
| 5 | 98 | 99 | 0 | 82 | 100 | 15 |
| 6 | 77 | 86 | 0 | 10 | 51 | 0 |
| 7 | 73 | 100 | 0 | 62 | 100 | 0 |
| 8 | 40 | 92 | 0 | 7 | 84 | 0 |
| 9 | 48 | 79 | 0 | 32 | 85 | 0 |
| 13 | 0 | 15 | 0 | 0 | 30 | 0 |
| 14 | 85 | 93 | 0 | 27 | 100 | 0 |
| 15 | 47 | 45 | 0 | 0 | 0 | 0 |
| 16 | 85 | 94 | 0 | 95 | 100 | 0 |
| 17 | 35 | 73 | 0 | 32 | 100 | 0 |
| 18 | 90 | 93 | 0 | 60 | 100 | 0 |
| 19 | 48 | 83 | 0 | 100 | 100 | 0 |
| 20 | 7 | 73 | 0 | 40 | 100 | 0 |
| 21 | 92 | 93 | 0 | 100 | 100 | 20 |
| 22 | 53 | 90 | 0 | 78 | 100 | 20 |
| 23 | 57 | 88 | 0 | 47 | 100 | 0 |
| 24 | 50 | 90 | 0 | 38 | 100 | 0 |
| 25 | 62 | 89 | 0 | 85 | 100 | 20 |
| 26 | 88 | 95 | 40 | 87 | 100 | 25 |
| 27 | 52 | 93 | 0 | 79 | 100 | 0 |
| 28 | 70 | 88 | 0 | 22 | 100 | 0 |
| 29 | 75 | 91 | 50 | 77 | 100 | 0 |
| 30 | 23 | 53 | 0 | 37 | 83 | 0 |
| 31 | 23 | 55 | 0 | 35 | 98 | 0 |
| 33 | 32 | 36 | 0 | 20 | 74 | 0 |
| 34 | 32 | 58 | 0 | 62 | 100 | 0 |
| 35 | 58 | 89 | 0 | 80 | 100 | 0 |
| 36 | 12 | 16 | 0 | 12 | 58 | 0 |
| 37 | 97 | 96 | 0 | 35 | 100 | 0 |
| 38 | 94 | 100 | 0 | 22 | 84 | 0 |
| 39 | 90 | 100 | 0 | 40 | 85 | 0 |
| 40 | 0 | 15 | — | 13 | 94 | 0 |
| 41 | 78 | 83 | 0 | 32 | 93 | 0 |
| 42 | 90 | 95 | 0 | 60 | 100 | 0 |
| 43 | 8 | 68 | 0 | 33 | 76 | 0 |
| 44 | 77 | 95 | 0 | 33 | 75 | 0 |
| 45 | 67 | 74 | 0 | 100 | 100 | 35 |
| 46 | 67 | 99 | 0 | 100 | 91 | 25 |
| 48 | 70 | 85 | 0 | 55 | 88 | 0 |
| 49 | 75 | 86 | 0 | 68 | 95 | 0 |
| 50 | 88 | 93 | 0 | 100 | 99 | 20 |
| 51 | 60 | 98 | 0 | 37 | 70 | 0 |
| 52 | 92 | 90 | 0 | 80 | 96 | 0 |
| 53 | 40 | 59 | 0 | 23 | 65 | 0 |
| 54 | 83 | 91 | 0 | 93 | 96 | 10 |
| 55 | 65 | 91 | 0 | 100 | 100 | 35 |
| 56 | 8 | 0 | 0 | 35 | 85 | 0 |
| 57 | 57 | 80 | 0 | 100 | 99 | 20 |
| 58 | 70 | 100 | 0 | 100 | 100 | 35 |
| 59 | 63 | 93 | 0 | 100 | 100 | 25 |
| 60 | 83 | 98 | 0 | 100 | 100 | 35 |
| 61 | 73 | 91 | 0 | 100 | 100 | 35 |
| 62 | 78 | 100 | 0 | 100 | 100 | 35 |
| 63 | 65 | 79 | 0 | 100 | 100 | 40 |
| 64 | 13 | 19 | 0 | 43 | 35 | 0 |
| 65 | 0 | 0 | 0 | 25 | 35 | — |
| 66 | 12 | 15 | 0 | 100 | 96 | — |
| 67 | 22 | 65 | 0 | 55 | 99 | — |
| 68 | 47 | 40 | 0 | 68 | 96 | 0 |
| 69 | 0 | 0 | 0 | 58 | 80 | 0 |
| 70 | 0 | 17 | 0 | 57 | 81 | 0 |
| 71 | 40 | 64 | 0 | 83 | 98 | 10 |
| 72 | 22 | 35 | 0 | 7 | 33 | 0 |
| 73 | 12 | 23 | 0 | 7 | 49 | 0 |
| 74 | 0 | 18 | 0 | 23 | 51 | — |
| 75 | 0 | 0 | 0 | 7 | 29 | — |
| 76 | 73 | 81 | 100 | 92 | 100 | 100 |
| 77 | 0 | 0 | 0 | 15 | 53 | 0 |
| 78 | 60 | 98 | — | 77 | 100 | 0 |
| 79 | 83 | 95 | 0 | 47 | 100 | — |
| 80 | 83 | 95 | 0 | 77 | 95 | — |
| 81 | 0 | 0 | 0 | 33 | 19 | 0 |
| 82 | 0 | 0 | 0 | 58 | 73 | 50 |
| 83 | 52 | 86 | 0 | 8 | 65 | 40 |
| 84 | 57 | 91 | 0 | 23 | 84 | 0 |
| 85 | 57 | 93 | 0 | 52 | 90 | 0 |
| 86 | 57 | 74 | 0 | 100 | 100 | 40 |
| 87 | 33 | 40 | 25 | 47 | 91 | 0 |
| 88 | 8 | 6 | 0 | 0 | 15 | 0 |
| 89 | 55 | 80 | 0 | 0 | 38 | 0 |
| 90 | 45 | 87 | 0 | 18 | 77 | 0 |
| 91 | 52 | 88 | 0 | 60 | 98 | 0 |
| 92 | 17 | 95 | 0 | 0 | 23 | 0 |
| 93 | 27 | 27 | 0 | 0 | 7 | 0 |
| 95 | 0 | 97 | 0 | 0 | 68 | 0 |
| 96 | 7 | 98 | 0 | 0 | 78 | 0 |
| 97 | 65 | 96 | 0 | 52 | 100 | 0 |
| 98 | 0 | 0 | 0 | 23 | 92 | 0 |
| 99 | 83 | 100 | 0 | 0 | 77 | 0 |
| 102 | 88 | 100 | 0 | 95 | 98 | 0 |
| 103 | 93 | 100 | 0 | 94 | 98 | 0 |
| 105 | 93 | 100 | 0 | 100 | 100 | 10 |
| 106 | 66 | 73 | 0 | 55 | 92 | 0 |
| 107 | 98 | 100 | 0 | 100 | 100 | 0 |
| 108 | 33 | 55 | — | 28 | 48 | 0 |
| 110 | 58 | 65 | 0 | 53 | 73 | 0 |
| 111 | 95 | 98 | 0 | 100 | 97 | 0 |
| 112 | 83 | 98 | 0 | 93 | 97 | 0 |
| 117 | 73 | 83 | 0 | 100 | 100 | 0 |
| 118 | 0 | 37 | 0 | 40 | 55 | 0 |
| 119 | 60 | 67 | 0 | 97 | 100 | 0 |
| 120 | 93 | 67 | 0 | 90 | 90 | 0 |
| 121 | 48 | 67 | 0 | 73 | 95 | 0 |
| 122 | 96 | 90 | 0 | 90 | 100 | 0 |
| 123 | 63 | 90 | 0 | 7 | 63 | 0 |
| 124 | 75 | 70 | 0 | 33 | 75 | 0 |
| 125 | 97 | 99 | 0 | 100 | 100 | 0 |
| 126 | 97 | 100 | 0 | 100 | 100 | 0 |
| 127 | 83 | 100 | 0 | 90 | 100 | 0 |
| 128 | 83 | 97 | 0 | 97 | 100 | 0 |
| 129 | 48 | 64 | 0 | 0 | 40 | 0 |
| 131 | 0 | 48 | 0 | 0 | 29 | 0 |
| 132 | 38 | 98 | 0 | 0 | 72 | 0 |
| 133 | 98 | 100 | 0 | 100 | 100 | 0 |
| 134 | 88 | 100 | 0 | 95 | 100 | 0 |
| 135 | 30 | 78 | 0 | 53 | 100 | 0 |
| 136 | 97 | 100 | 0 | 100 | 100 | 0 |
| 139 | 100 | 100 | 0 | 92 | 100 | 0 |
| 140 | 43 | 68 | 0 | 0 | 98 | 0 |
| 141 | 85 | 80 | 0 | 53 | 100 | 0 |
| 142 | 37 | 65 | 0 | 0 | 74 | 0 |

Compounds 13, 65, 72, 75, 81 and 93 each showed limited overall activity against weeds in the above tables. The following Tables III and IV are included to show activity against specific weeds used in the above tests.

TABLE III

| Cmpd. No. | Pre-Emergence Control | | | | | | | |
|---|---|---|---|---|---|---|---|---|
| | FT | WG | WO | AMG | VL | MD | CD | YNS |
| 13 | 0 | 0 | 0 | 0 | 30 | 30 | 0 | 0 |
| 65 | 0 | 0 | 0 | 0 | 0 | 0 | 0 | 0 |
| 72 | 20 | 20 | 25 | 20 | 0 | 40 | 80 | 0 |
| 75 | 0 | 0 | 0 | 0 | 0 | 0 | 0 | 0 |
| 81 | 0 | 0 | 0 | 0 | 0 | 0 | 0 | 0 |
| 93 | 80 | 0 | 0 | 0 | 0 | 80 | — | 0 |

TABLE IV

| Cmpd. No. | Post-Emergence Control | | | | | | | | |
|---|---|---|---|---|---|---|---|---|---|
| | FT | WG | WO | AMG | VL | MD | CD | YNS | TOM |
| 13 | 0 | 0 | 0 | 0 | 60 | 60 | 0 | 0 | — |
| 65 | 35 | 30 | 10 | 20 | 25 | 45 | 50 | — | — |
| 72 | 0 | 20 | 0 | 25 | 30 | 35 | 40 | 0 | 90 |
| 75 | 10 | 10 | 0 | 35 | 50 | 30 | 0 | — | — |
| 81 | 75 | 25 | 0 | 0 | 0 | 25 | 50 | 0 | — |
| 93 | 0 | 0 | 0 | 5 | 10 | 5 | — | 0 | — |

Compounds not depicted in the foregoing Tables II, III and IV and the following Tables VII and VIII were tested according to the following pre- and postemergence multi-weed/multi-crop evaluations.

Pre-Emergence Multi-weed/Multi-crop Evaluation

Compounds were variously evaluated at application rates of 0.1, 0.25, 0.5, 1.0 and 2.0 pounds active ingredient/acre (0.112, 0.28, 0.56, 1.12 and 2.24 kg/ha, respectively) for pre-emergence activity against a number of weed and crop species. The procedure was generally similar to the pre-emergence evaluation described above. Weed species utilized were as follows: grassy weeds—downy brome (*Bromus tectorum*), foxtail (*Setaria sp*), annual ryegrass (*Lolium multiflorum*), watergrass (*Echinochloa crusgalli*), shattercane (*Sorghum bicolor*), wild oats (*Avena fatua*); and broadleaf signalgrass (*Brachiaria platyphylla*): broadleaf weeds—annual morningglory (*Ipomoea purpurea*), sesbania (*Sesbania sp.*), velvetleaf (*Abutilon theophrasti*), sicklepod (*Cassia obtusifolia*) and mustard (*Brassica sp.*). Yellow nutsedge (*Cyperus esculentus*) was also included in these tests. Crops included were: soybean (*Glycine max*), rice (*Oryza sativa*), cotton (*Gossypium herbaceum*), corn (*Zea mays*), wheat (*Triticum aestivum*), milo (*Sorghum vulgare*) and sugarbeets (*Beta vulgaris*).

The following Table V contains the results of these tests, in terms of average control of the five broadleaf weeds, seven grassy weeds, and nutsedge, and injury to the crop species, with visual ratings ranging from 0% (no injury) to 100% (complete kill) as compared to untreated control flat; (—) indicates the compound was not tested.

TABLE V

| Cmpd. No. | Rate lb/A | Broad leaf- weeds | Grasses | Nut- sedge | Soy- bean | Corn | Rice | Cotton | Wheat | Milo | Sugar- beets |
|---|---|---|---|---|---|---|---|---|---|---|---|
| 10 | 2.00 | 53 | 0 | 0 | 0 | 0 | 0 | 0 | 0 | 0 | 0 |
| | 1.00 | 18 | 0 | 0 | 0 | 0 | 0 | 0 | 0 | 0 | 0 |
| | 0.50 | 0 | 0 | 0 | 0 | 0 | 0 | 0 | 0 | 0 | 0 |
| | 0.25 | 0 | 0 | 0 | 0 | 0 | 0 | 0 | 0 | 0 | 0 |
| 11 | 2.00 | 33 | 14 | 0 | 0 | 0 | 0 | 0 | 0 | 0 | 0 |
| | 1.00 | 15 | 3 | 0 | 0 | 0 | 0 | 0 | 0 | 0 | 0 |
| | 0.50 | 0 | 0 | 0 | 0 | 0 | 0 | 0 | 0 | 0 | 0 |
| | 0.25 | 0 | 0 | 0 | 0 | 0 | 0 | 0 | 0 | 0 | 0 |
| 12 | 2.00 | 96 | 82 | 15 | 100 | 30 | 35 | 20 | 20 | 15 | 100 |
| | 1.00 | 95 | 52 | 0 | 100 | 15 | 35 | 0 | 10 | 10 | 95 |
| | 0.50 | 60 | 24 | 0 | 17 | 0 | 15 | 0 | 0 | 10 | 95 |
| | 0.25 | 13 | — | 0 | 15 | 0 | 10 | 0 | 0 | 0 | 0 |
| 32 | 2.00 | 43 | 14 | 0 | 40 | 10 | 0 | 50 | 0 | 35 | 90 |
| | 1.00 | 17 | 2 | 0 | 15 | 0 | 0 | 30 | 0 | 10 | 90 |
| | 0.50 | 0 | 0 | 0 | 0 | 0 | 0 | 10 | 0 | 10 | 0 |
| | 0.25 | 0 | 0 | 0 | 0 | 0 | 0 | 0 | 0 | 0 | 0 |
| 47 | 2.00 | 100 | 73 | 0 | 65 | 20 | 0 | 20 | 0 | 30 | 100 |
| | 1.00 | 98 | 60 | 0 | 55 | 0 | 0 | 0 | 0 | 15 | 100 |
| | 0.50 | 81 | — | 0 | 30 | 0 | 0 | 0 | 0 | 0 | 70 |
| 94 | 1.00 | 46 | 12 | 0 | 0 | 25 | 35 | 0 | 0 | 0 | 75 |
| | 0.50 | 71 | 23 | 0 | 40 | 40 | 35 | 0 | 20 | 25 | 100 |
| | 0.25 | 63 | — | 0 | 35 | 20 | 20 | 0 | 0 | 0 | 70 |
| | 0.13 | 43 | — | 0 | 90 | 35 | 0 | 25 | 0 | 0 | 50 |
| 100 | 2.00 | 86 | 72 | 0 | 50 | 35 | 35 | 0 | 10 | 10 | 100 |
| | 1.00 | 59 | 49 | 0 | 10 | 15 | 5 | 0 | 10 | 0 | 90 |
| | 0.50 | 30 | 30 | 0 | 0 | 0 | 0 | 0 | 0 | 0 | 20 |
| | 0.25 | 5 | 19 | 0 | 20 | 20 | 25 | 20 | 0 | 0 | 20 |
| 101 | 2.00 | 64 | 3 | 0 | 30 | 0 | 0 | 0 | 0 | 0 | 80 |
| | 1.00 | 55 | 0 | 0 | 0 | 0 | 0 | 0 | 0 | 0 | 80 |
| | 0.50 | 37 | 0 | 0 | 0 | 0 | 0 | 0 | 0 | 0 | 60 |
| | 0.25 | 22 | 0 | 0 | 0 | 0 | 0 | 0 | 0 | 0 | 0 |
| 104 | 2.00 | 63 | 53 | 0 | 40 | 0 | 15 | 0 | 10 | 25 | 50 |
| | 1.00 | 35 | 21 | 0 | 80 | 0 | 20 | 0 | 0 | 0 | 25 |
| | 0.50 | 15 | 0 | 0 | 0 | 0 | 0 | 0 | 0 | 0 | 0 |
| 130 | 2.00 | 0 | 0 | 0 | 0 | 0 | 0 | 0 | 0 | 0 | 0 |

TABLE V-continued

| Cmpd. No. | Rate lb/A | Broad leaf-weeds | Grasses | Nut-sedge | Soy-bean | Corn | Rice | Cotton | Wheat | Milo | Sugar-beets |
|---|---|---|---|---|---|---|---|---|---|---|---|
|  | 1.00 | 0 | 0 | 0 | 0 | 0 | 0 | 0 | 0 | 0 | 0 |
| 137 | 1.00 | 97 | 48 | 0 | 80 | 0 | 20 | 0 | 0 | 10 | 100 |
|  | 0.50 | 60 | 12 | 0 | 60 | 0 | 10 | 0 | 0 | 0 | 80 |
|  | 0.25 | 35 | 0 | 0 | 40 | 0 | 0 | 0 | 0 | 0 | 5 |
| 138 | 2.00 | 99 | 87 | 0 | 95 | 40 | 60 | 0 | 60 | 50 | 95 |
|  | 1.00 | 85 | 40 | 0 | 90 | 20 | 40 | 10 | 10 | 20 | 99 |
|  | 0.50 | 55 | 18 | 0 | 60 | 0 | 20 | 0 | 10 | 15 | 95 |

Post-Emergence Multi-weed/Multi-crop Evaluation

Compounds were variously evaluated at application rates of 0.1, 0.25, 0.5, 1.0 and 2.0 pounds active ingredient/acre (0.112, 0.28, 0.56, 1.12 and 2.24 kg/ha, respectively) for post-emergence activity against a number of weed and crop species. The procedure was generally similar to the pre-emergence evaluation described above; the same weed and crop species were utilized.

The following Table VI contains the results of these tests, in terms of average control of the six broadleaf weeds, six grassy weeds, and nutsedge, and injury to the crop species, with visual ratings ranging from 0% (no injury) to 100% (complete kill) as compared to untreated control flat; (—) indicates the compound was not tested.

TABLE VI

| Cmpd. No. | Rate lb/A | Broad leaf-weeds | Grasses | Nut-sedge | Soy-bean | Corn | Rice | Cotton | Wheat | Milo | Sugar-beets |
|---|---|---|---|---|---|---|---|---|---|---|---|
| 10 | 2.00 | 12 | 0 | 0 | 0 | 0 | 0 | 0 | 0 | 0 | 0 |
|  | 1.00 | 0 | 0 | 0 | 0 | 0 | 0 | 0 | 0 | 0 | 0 |
|  | 0.50 | 0 | 0 | 0 | 0 | 0 | 0 | 0 | 0 | 0 | 0 |
|  | 0.25 | 0 | 0 | 0 | 0 | 0 | 0 | 0 | 0 | 0 | 0 |
|  | 0.10 | 0 | — | 0 | 0 | 0 | 0 | 0 | 0 | 0 | 0 |
| 11 | 2.00 | 10 | 3 | 0 | 0 | 0 | 0 | 0 | 0 | 0 | 0 |
|  | 1.00 | 0 | 0 | 0 | 0 | 0 | 0 | 0 | 0 | 0 | 0 |
|  | 0.50 | 0 | 0 | 0 | 0 | 0 | 0 | 0 | 0 | 0 | 0 |
|  | 0.25 | 0 | 0 | 0 | 0 | 0 | 0 | 0 | 0 | 0 | 0 |
|  | 0.10 | 0 | — | 0 | 0 | 0 | 0 | 0 | 0 | 0 | 0 |
| 12 | 2.00 | 91 | 31 | 0 | 100 | 25 | 50 | 0 | 25 | 15 | 90 |
|  | 1.00 | 73 | 6 | 0 | 75 | 10 | 15 | 0 | 0 | 0 | 60 |
|  | 0.50 | 58 | 0 | 0 | 75 | 0 | 0 | 0 | 0 | 0 | 60 |
|  | 0.25 | 34 | 0 | 0 | 65 | 0 | 0 | 0 | 0 | 0 | 60 |
|  | 0.10 | 15 | — | 0 | 20 | 0 | 0 | 0 | 0 | 0 | 55 |
| 32 | 2.00 | 29 | 16 | 0 | 20 | 0 | 20 | 60 | 0 | 15 | 20 |
|  | 1.00 | 24 | 4 | 0 | 10 | 0 | 0 | 30 | 0 | 10 | 0 |
|  | 0.50 | 12 | 0 | 0 | 10 | 0 | 0 | 15 | 0 | 10 | 0 |
|  | 0.25 | 2 | 0 | 0 | 0 | 0 | 0 | 0 | 0 | 0 | 0 |
| 47 | 2.00 | 100 | 65 | 0 | 100 | 40 | 50 | 35 | 35 | 40 | 100 |
|  | 1.00 | 96 | 24 | 0 | 90 | 20 | 25 | 90 | 20 | 15 | 100 |
|  | 0.50 | 92 | — | 0 | 100 | 0 | 30 | 40 | 20 | — | 100 |
| 94 | 1.00 | 46 | 0 | 0 | 75 | 35 | 25 | 15 | 0 | 0 | 100 |
|  | 0.50 | 53 | 13 | 0 | 100 | 0 | 75 | 15 | 30 | 0 | 100 |
|  | 0.25 | 60 | — | 0 | 60 | 0 | 75 | 25 | 10 | 0 | 100 |
|  | 0.13 | 59 | — | 0 | 25 | 0 | 50 | 0 | 15 | 0 | 100 |
| 100 | 2.00 | 100 | 76 | 100 | 100 | 25 | 0 | 40 | 10 | 10 | 100 |
|  | 1.00 | 100 | 26 | 0 | 50 | 10 | 15 | 20 | 10 | 15 | 90 |
|  | 0.50 | 48 | 0 | 0 | 60 | 0 | 0 | 0 | 0 | 0 | 50 |
|  | 0.25 | 23 | 0 | 0 | 35 | 0 | 0 | 0 | 0 | 0 | 50 |
| 101 | 2.00 | 89 | 12 | 5 | 10 | 0 | 0 | 20 | 10 | 0 | 95 |
|  | 1.00 | 25 | 0 | 10 | 20 | 0 | 0 | 0 | 15 | 0 | 40 |
|  | 0.50 | 20 | 0 | 10 | 10 | 0 | 0 | 0 | 10 | 0 | 40 |
|  | 0.25 | 0 | 0 | 0 | 0 | 0 | 0 | 0 | 0 | 0 | 20 |
| 104 | 2.00 | 93 | 68 | 0 | 50 | 25 | 25 | 20 | 0 | 10 | 85 |
|  | 1.00 | 79 | 60 | 0 | 30 | 20 | 10 | 15 | 0 | 0 | 25 |
|  | 0.50 | 46 | 20 | 0 | 60 | 0 | 25 | 10 | 0 | 15 | 35 |
| 130 | 2.00 | 30 | 6 | 0 | 60 | 0 | 0 | 15 | 0 | 10 | 40 |
|  | 1.00 | 16 | 0 | 0 | 100 | 0 | 0 | 15 | 0 | 0 | 0 |
| 137 | 1.00 | 83 | 23 | 0 | 90 | 0 | 40 | 0 | 25 | 10 | 100 |
|  | 0.50 | 70 | 2 | 0 | 40 | 0 | 15 | 0 | 10 | 10 | — |
|  | 0.25 | 28 | 3 | 0 | 20 | 0 | 10 | 10 | 10 | 0 | 90 |
| 138 | 2.00 | 100 | 63 | 10 | 100 | 0 | 90 | 20 | 60 | 15 | 100 |
|  | 1.00 | 99 | 39 | 0 | 95 | 0 | 30 | 10 | 20 | 15 | 100 |
|  | 0.50 | 79 | 20 | 0 | 80 | 0 | 15 | 0 | 10 | 0 | 98 |

Compounds not depicted in the foregoing Tables II, III, IV, V and VI were tested according to the following pre- and post-emergence controlled light evaluation.

Controlled Light—Pre-emergence Multi-Weed/Multi-Crop Evaluation

Flats were filled with sandy loam soil containing a fungicide. The soil was leveled and rows of 4 grassy weeds, 5 broadleaf weeds and three crops were planted thickly enough so that several seedlings emerged per inch of row. Grassy weeds utilized were blackgrass (*Alopecurus myosuroides*), perennial ryegrass (*Lolium perenne*), wild oats (*Avena fatua*) and poverty brome (*Bromus sterilis*). Broadleaf weeds utilized were scented mayweed (*Matricaria recutita*), common chickweed (*Stellaria media*), bedstraw (*Galium aparine*), carrot (*Daucus carota*) and wild mustard (*Brassica kaber*). Crops utilized were sugarbeet (*Beta vulgaris*), barley (*Hordeum vulgare*) and wheat (*Triticum aestivum*).

After seeding, the flats were immediately sprayed with solutions of the selected test compounds at a rate of 40 gallons of solution per acre with the compound being applied at a rate of 2 pounds per acre (2.24 kg/ha).

The solutions of the test compounds were made by weighing 240 mg of the test compound into a 60 ml wide-mouth bottle, dissolving it in 20 ml of acetone containing 0.5% polyoxyethylene sorbitan monolaurate emulsifier and then brought to volume with 20 ml of water.

The flats were placed in a greenhouse with whitewash maintained on the glazing to reduce light intensity to approximately one-half sunlight and in which the temperature was maintained between 15°-24° C.

The degree of control was estimated and recorded from 3-4 weeks after treatment as percentage compared to the growth of the same species in an untreated flat of the same age. Percent control was based on the total injury to the plants due to all factors including inhibited germination, killing of the plant tissue adter emergence, stunting, malformation, chlorosis and other types of injury. The control ratings ranged from 0-100 percent, with 0 representing no effect with growth equal to the untreated control, and 100 representing complete kill.

The following Table VII contains the results of these tests in terms of average control of the four grasses, five broadleaf weeds annd three crops in these evaluations.

TABLE VII

| Cmpd. No. | Rate lb/A | Average Grasses | Pre-Emergence Average Broadleaf | Sugar-beet | Barley | Wheat |
| --- | --- | --- | --- | --- | --- | --- |
| 109 | 2.00 | 5 | 30 | 40 | 20 | 25 |
| 113 | 2.00 | 13 | 32 | 0 | 0 | 0 |
| 114 | 2.00 | 14 | 47 | 0 | 0 | 0 |
| 115 | 2.00 | 13 | 35 | 15 | 0 | 0 |
| 116 | 2.00 | 16 | 31 | 10 | 0 | 0 |

Controlled Light Post-emergence
Multi-Weed/Multi-Crop Evaluation

The soil was prepared and seeded as described for the pre-emergence test. Flats containing seeds of broadleaf species were placed in the greenhouse 21 days, and flats containing seeds of grass species were placed in the greenhouse 14 days before spraying at the same rates as in the pre-emergence evaluation.

After spraying, the flats were returned to the greenhouse and watered daily. Three to four weeks after treatment, the degree of control was estimated and the percent control ratings were assigned on the same basis as for the pre-emergence evaluation.

The following Table VIII contains the results of these tests in terms of average control of the four grasses, five broadleaf weeds and three crops in these evaluations.

TABLE VIII

| Cmpd. No. | Rate lb/A | Average Grasses | Post-Emergence Average Broadleaf | Sugar-beet | Barley | Wheat |
| --- | --- | --- | --- | --- | --- | --- |
| 109 | 2.00 | 49 | 76 | 95 | 35 | 20 |
| 113 | 2.00 | 76 | 88 | 100 | 30 | 20 |
| 114 | 2.00 | 53 | 66 | 100 | 35 | 20 |
| 115 | 2.00 | 69 | 84 | 100 | 40 | 30 |
| 116 | 2.00 | 76 | 86 | 100 | 30 | 15 |

Formulations

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, microcapsules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives, thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention, as well as materials in their naturally occurring form. Examples of such carriers are vermiculite, sintered clay granules, kaolin, attapulgite clay, sawdust and granular carbon. Useful encapsulating materials include natural and synthetic rubbers, cellulosic materials, styrene-butadiene copolymers, polyacrylonitriles, polyacrylates, polyesters, polyamides, polyureas, polyurethanes and starch xanthates.

Wettable powders, flowables, and pastes are obtained by mixing and grinding an active compound with one or more dispensing agents and/or solid carriers or diluents. Also included may be wetting agents and/or dispersing agents, for example, lignins, methyl cellulose, naphthalenedsulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—1 to 90% active compound; aqueous suspensions—10 to 50% active compound; dusts and powders—1 to 25% active compound; granules and pellets—0.5 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of powder dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Ingredient | Weight % | | |
|---|---|---|---|
| Oil | | | |
| Compound 1 | 1 | | |
| Oil solvent heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |

| Ingredient | Wt. % | Wt. % | Wt. % |
|---|---|---|---|
| Dusts and/or Powders | | | |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. A compound having the formula

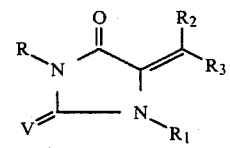

wherein R is $C_1$-$C_6$ alkyl, phenyl, phenyl substituted with one or more $C_1$-$C_4$ alkyl, $C_1$-$C_4$ alkylsulfonyl, $C_1$-$C_4$ alkoxy, halo, or $C_1$-$C_4$ haloalkyl;
$R_1$ is hydrogen, $C_1$-$C_3$ alkyl, phenyl or phenyl substituted with halo or $C_1$-$C_6$ alkyl;
$R_2$ is hydrogen or $C_1$-$C_3$ alkyl;
$R_3$ is

wherein $R_4$ and $R_5$ are independently hydrogen, $C_1$-$C_6$ alkyl, phenyl, halophenyl, phenalkyl, alkylphenalkyl, halophenalkyl, cycloalkyl, cycloalkylmethyl, naphthyl, pyridyl, pyridylalkyl, or $R_4$ and $R_5$ taken together with nitrogen form hexamethyleneimine, piperidine, phenylpiperidine, benzylpiperidine, indoline, or perhydroindoline; and V is sulfur or oxygen; provided that when R is $C_1$–$C_6$ alkyl, $R_1$ is phenyl or phenyl substituted with one or more halo or $C_1$–$C_6$ alkyl and $R_4$ is alkyl or hydrogen and when R is phenyl or phenyl substituted with one or more $C_1$–$C_4$ alkyl, $C_1$–$C_4$ alkoxy, halo or $C_1$–$C_4$ haloalkyl and $R_4$ is alkyl or hydrogen, then $R_5$ is other than alkyl or hydrogen; and provided that when $R_1$ is methyl and $R_3$ is

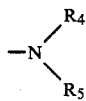

wherein $R_4$ is methyl and $R_5$ is phenyl, then R is other than 2-chlorophenyl or 2-methoxyphenyl; and when $R_1$ is hydrogen or ethyl and $R_3$ is

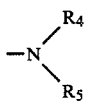

wherein $R_4$ is methyl and $R_5$ is phenyl, then R is other than 3,4-dichlorophenyl.

2. A compound according to claim 1 wherein R is methyl; $R_1$ is phenyl substituted with halo, alkyl or combinations thereof; $R_2$ is hydrogen; $R_3$ is a group having the formula

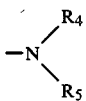

wherein $R_4$ is methyl; $R_5$ is phenylalkyl or phenyl and V is oxygen.

3. A compound according to claim 2 wherein $R_1$ is halophenyl or alkylhalophenyl, and $R_5$ is phenyl or phenalkyl.

4. A compound according to claim 3 wherein $R_1$ is 2-fluorophenyl, 2,5-difluorophenyl or 2-fluoro-4-methylphenyl.

5. A compound according to claim 1 wherein R is phenyl, phenyl substituted with halo, alkyl, haloalkyl or combinations thereof, $R_1$ is alkyl; $R_2$ is hydrogen or methyl, $R_3$ is a group having the formula

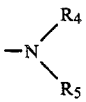

wherein $R_4$ and $R_5$ are independently hydrogen, alkyl, phenyl, halophenyl, benzyl, phenalkyl, pyridyl or pyridylalkyl and V is oxygen provided that when $R_4$ is alkyl, then $R_5$ is other than alkyl or hydrogen.

6. A compound according to claim 5 wherein R is phenyl, 2-fluorophenyl, 3-fluorophenyl, 4-fluorophenyl, 2,4-difluorophenyl, 2,5-difluorophenyl, 2-fluoro-4-bromophenyl, 4-fluoro-3-chlorophenyl, 2-fluoro-4-chlorophenyl, 2-fluoro-4-methylphenyl, 2-chlorophenyl, 3-chlorophenyl, 4-chlorophenyl, 3,4-dichlorophenyl, 3-chloro-4-methylphenyl or 4-methylphenyl; $R_1$ is methyl; $R_4$ is methyl and $R_5$ is phenyl.

7. A compound according to claim 6 wherein $R_2$ is hydrogen.

8. A compound according to claim 7 wherein R is 2,5-difluorophenyl.

9. A compound according to claim 7 wherein R is 2-fluoro-4-methylphenyl.

10. A compound according to claim 5 wherein R is phenyl, halophenyl or haloalkylphenyl, $R_1$ is methyl, $R_2$ is hydrogen, $R_4$ is hydrogen or methyl and $R_5$ is halophenyl.

11. A compound according to claim 10 wherein R is 4-chlorophenyl, 3-trifluoromethylphenyl or 2,5-difluorophenyl; $R_4$ is methyl and $R_5$ is halophenyl.

12. A compound according to claim 10 wherein R is phenyl or 3,4-dichlorophenyl; $R_4$ is hydrogen and $R_5$ is halophenyl.

13. A compound according to claim 5 wherein R is phenyl, 2-fluorophenyl, 3-fluorophenyl, 2,3-difluorophenyl, 2,4-difluorophenyl, 2,5-difluorophenyl, 2,6-difluorophenyl, 2-fluoro-5-chlorophenyl, 4-fluoro-3-chlorophenyl, 4-fluoro-3-trifluoromethylphenyl, 2-fluoro-4-methylphenyl, 3-fluoro-4-methylphenyl, 3-chlorophenyl, 4-chlorophenyl, 3,4-dichlorophenyl, 2,6-dichlorophenyl, 3-chloro-5-methylphenyl or 4-methylphenyl; $R_1$ is methyl; $R_4$ is methyl and $R_5$ is benzyl.

14. A compound according to claim 13 wherein $R_2$ is hydrogen.

15. A compound according to claim 14 wherein R is 2,5-difluorophenyl.

16. A compound according to claim 14 wherein R is 2-fluoro-4-methylphenyl.

17. A compound according to claim 5 wherein R is 2-fluorophenyl, 2,6-difluorophenyl, 2-fluoro-3-chlorophenyl, 2-fluoro-4-methylphenyl, 3-fluoro-4-methylphenyl, 4-fluoro-3-trifluoromethylphenyl, 2-fluoro-4-bromophenyl, 2,5-difluoro-4-methylphenyl, 3-chlorophenyl, 3-chloro-4-methylphenyl, 4-methylphenyl, 3-iodophenyl or 4-bromophenyl; $R_1$ is methyl; $R_4$ is methyl and $R_5$ is phenethyl.

18. A compound according to claim 17 wherein $R_2$ is hydrogen.

19. A compound according to claim 18 wherein R is 2,5-difluorophenyl.

20. A compound according to claim 18 wherein R is 2-fluoro-4-methylphenyl.

21. A compound according to claim 18 wherein R is 2,5-difluoro-4-methylphenyl.

22. A compound according to claim 5 wherein R is phenyl, 2-fluorophenyl, 4-fluorophenyl, 2-fluoro-4-methylphenyl or 4-chlorophenyl; $R_1$ is methyl; $R_4$ is ethyl and $R_5$ is phenyl.

23. A compound according to claim 5 wherein R is 2-fluorophenyl; $R_1$ is methyl; $R_4$ is isopropyl and $R_5$ is phenyl or phenalkyl.

24. A compound according to claim 5 wherein $R_2$ is hydrogen, $R_4$ is methyl; $R_5$ is phenyl or phenalkyl and V is sulfur.

25. A compound according to claim 1 wherein R is halophenyl; $R_2$ is alkyl; $R_4$ is $C_1$–$C_4$ lower alkyl and $R_5$ is phenyl or phenalkyl.

26. A compound according to claim 25 wherein R is 2-fluorophenyl; $R_1$ is methyl; $R_2$ is methyl; $R_4$ is methyl and $R_5$ is phenyl or benzyl.

27. A compound according to claim 1 wherein R is phenyl or halophenyl; $R_1$ is methyl; $R_2$ is hydrogen and $R_4$ and $R_5$ are independently $C_1$–$C_4$ alkyl, cycloalkyl, pyridyl, pyridylalkyl, phenalkyl, naphthyl, phenyl or halophenyl.

28. A compound according to claim 27 wherein R is halophenyl; $R_4$ is $C_1$-$C_4$ alkyl and $R_5$ is benzyl.

29. A compound according to claim 28 wherein R is halophenyl; $R_4$ is benzyl and $R_5$ is benzyl.

30. A compound according to claim 1 wherein R is phenyl or halophenyl; $R_1$ is $C_1$-$C_3$ alkyl; $R_2$ is hydrogen or methyl; $R_4$ and $R_5$ taken together with nitrogen form hexamethyleneimine, piperidine, phenylpiperidine, benzylpiperadine, indoline, or perhydroindole and V is oxygen.

31. A compound according to claim 1 wherein R is phenyl substituted with halo or alkyl, $R_1$ is ethyl; $R_2$ is hydrogen; $R_4$ is methyl; $R_5$ is phenyl and V is oxygen.

32. A compound according to claim 1 wherein R is phenyl, 4-chlorophenyl, 3-chloro-4-fluorophenyl, 3-chloro-4-methylphenyl, 3-methylphenyl, 3-methoxyphenyl, 4-methylphenyl, 4-methoxyphenyl, 3-methanesulfonylphenyl, 2-fluorophenyl, 3-fluorophenyl, 4-fluorophenyl, 2,3-difluorophenyl, 2,4-difluorophenyl, 2,5-difluorophenyl, 2-fluoro-4-chlorophenyl, 2-fluoro-4-bromophenyl, 3-fluoro-4-methylphenyl, 2-trifluoromethylphenyl, 3-trifluoromethylphenyl, 4-trifluoromethylphenyl or 3-trifluoromethyl-4-fluorophenyl; $R_1$ is methyl; $R_2$ is hydrogen; $R_4$ is methyl; $R_5$ is phenyl and V is oxygen.

33. A compound according to claim 1 wherein R is phenyl, 4-methylphenyl, 4-methoxyphenyl, 4-bromophenyl, 3-iodophenyl, 3-chlorophenyl, 4-chlorophenyl, 3,4-dichlorophenyl, 3,5-dichlorophenyl, 3-chloro-4-methylphenyl, 3-chloro-4-fluorophenyl, 2-fluorophenyl, 3-fluorophenyl, 2,3-difluorophenyl, 2,4-difluorophenyl, 2,5-difluorophenyl, 2,6-difluorophenyl, 2-fluoro-4-bromophenyl, 2-fluoro-3-chlorophenyl, 2-fluoro-4-chlorophenyl, 2-fluoro-5-chlorophenyl, 2-fluoro-4-chloro-5-methoxyphenyl, 2,5-difluoro-4-methylphenyl, 2-fluoro-4-methylphenyl, 3-fluoro-4-methylphenyl, 2-fluoro-4methoxyphenyl, 2-fluoro-5-trifluoromethylphenyl, 2-trifluoromethylphenyl, 3-trifluoromethylphenyl, 4-trifluoromethylphenyl, or 3-trifluoromethyl-4-fluorophenyl; $R_1$ is methyl; $R_2$ is hydrogen; $R_4$ is hydrogen, methyl, ethyl, isopropyl, or butyl; $R_5$ is benzyl, 2-chlorobenzyl, 3-chlorobenzyl, 4-chlorobenzyl, phenethyl, or phenpropyl and V is oxygen.

34. A compound according to claim 5 wherein R is phenyl or halophenyl; $R_1$ is $C_1$-$C_3$ lower alkyl; $R_2$ is hydrogen; $R_4$ is methyl; $R_5$ is 2-pyridyl or 2-pyridylalkyl and V is oxygen.

35. A compound according to claim 34 wherein $R_1$ is methyl and $R_5$ is 2-pyridylethyl.

36. A compound according to claim 35 wherein R is 2-fluoro-4-methylphenyl.

37. A compound according to claim 1 wherein R is phenyl or halophenyl; $R_1$ is $C_1$-$C_3$ lower alkyl; $R_2$ is hydrogen; $R_4$ is $C_1$-$C_4$ alkyl; $R_5$ is $C_3$-$C_6$ cycloalkyl or $C_3$-$C_6$ alkylcycloalkyl and V is oxygen.

38. A compound according to claim 37 wherein $R_5$ is cyclohexyl.

39. A compound according to claim 37 wherein R is phenyl, 2-fluorophenyl, 2,5-difluorophenyl, 3-chlorophenyl or 3,4-dichlorophenyl; $R_1$ is methyl and $R_4$ is methyl or ethyl.

40. A compound according to claim 37 wherein R is halophenyl and $R_5$ is cyclopropylmethyl.

41. A method of controlling undesirable vegetation comprising applying to said vegetation or the locus thereof, an herbicidally effective amount of a compound having the formula

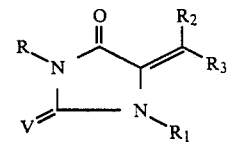

wherein R is $C_1$-$C_6$ alkyl, phenyl, phenyl substituted with one or more $C_1$-$C_4$ alkyl, $C_1$-$C_4$ alkylsulfonyl, $C_1$-$C_4$ alkoxy, halo, or $C_1$-$C_4$ haloalkyl;
$R_1$ is hydrogen, $C_1$-$C_3$ alkyl, phenyl or phenyl substituted with halo or $C_1$-$C_6$ alkyl;
$R_2$ is hydrogen or $C_1$-$C_3$ alkyl;
$R_3$ is

wherein $R_4$ and $R_5$ are independently hydrogen, $C_1$-$C_6$ alkyl, phenyl, halophenyl, phenalkyl, alkylphenalkyl, halophenalkyl, cycloalkyl, cycloalkylmethyl, naphthyl, pyridyl, pyridylalkyl, or $R_4$ and $R_5$ taken together with nitrogen form hexamethyleneimine, piperidine, phenylpiperidine, benzylpiperidine, indoline, or perhydroindoline; and
V is sulfur or oxygen;
provided that when R is $C_1$-$C_6$ alkyl, $R_1$ is phenyl or phenyl substituted with one or more halo or $C_1$-$C_6$ alkyl and $R_4$ is alkyl or hydrogen and when R is phenyl or phenyl substituted with one or more $C_1$-$C_4$ alkyl, $C_1$-$C_4$ alkoxy, halo or $C_1$-$C_4$ haloalkyl and $R_4$ is alkyl or hydrogen, then $R_5$ is other than alkyl or hydrogen; and provided that when $R_1$ is methyl and $R_3$ is

wherein $R_4$ is methyl and $R_5$ is phenyl, then R is other than 2-chlorophenyl or 2-methoxyphenyl; and when $R_1$ is hydrogen or ethyl and $R_3$ is

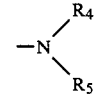

wherein $R_4$ is methyl and $R_5$ is phenyl, then R is other than 3,4-dichlorophenyl.

42. The method of claim 41 wherein R is methyl, $R_1$ is phenyl substituted with halo, alkyl or combinations thereof; $R_2$ is hydrogen; $R_3$ is a group having the formula

wherein $R_4$ is methyl; $R_5$ is phenalkyl or phenyl and V is oxygen.

43. The method of claim 42 wherein $R_1$ is halophenyl or alkylphenyl.

44. The method of claim 43 wherein $R_1$ is 2-fluorophenyl, 2,5-difluorophenyl or 2-fluoro-4-methylphenyl.

45. The method of claim 44 wherein R is phenyl, phenyl substituted with halo, alkyl, haloalkyl or combinations thereof, $R_1$ is alkyl; $R_2$ is hydrogen or methyl; $R_3$ is a group having the formula

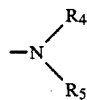

wherein $R_4$ and $R_5$ is independently hydrogen, alkyl, phenyl, halophenyl, benzyl, phenalkyl, pyridyl or pyridylalkyl and V is oxygen provided that when $R_4$ is alkyl, then $R_5$ is other than alkyl or hydrogen.

46. The method of claim 45 wherein R is phenyl, 2-fluorophenyl, 3-fluorophenyl, 4-fluorophenyl, 2,4-difluorophenyl, 2,5-difluorophenyl, 2-fluoro-4-bromophenyl, 4-fluoro-3-chlorophenyl, 2-fluoro-4-chlorophenyl, 2-fluoro-4-methylphenyl, 2-chlorophenyl, 3-chlorophenyl, 4-chlorophenyl, 3,4-dichlorophenyl, 3-chloro-4-methylphenyl or 4-methylphenyl; $R_1$ is methyl; $R_4$ is methyl and $R_5$ is phenyl.

47. The method of claim 46 wherein $R_2$ is hydrogen.

48. The method of claim 47 wherein R is 2,5-difluorophenyl.

49. The method of claim 47 wherein R is 2-fluoro-4-methylphenyl.

50. The method of claim 45 wherein R is phenyl, halophenyl or haloalkylphenyl, $R_1$ is methyl, $R_2$ is hydrogen, $R_4$ is hydrogen or methyl and $R_5$ is halophenyl.

51. The method of claim 50 wherein R is 4-chlorophenyl, 3-trifluoromethylphenyl or 2,5-difluorophenyl; $R_4$ is methyl and $R_5$ is halophenyl.

52. The method of claim 50 wherein R is phenyl or 3,4-dichlorophenyl; $R_4$ is hydrogen and $R_5$ is halophenyl.

53. The method of claim 45 wherein R is phenyl, 2-fluorophenyl, 3-fluorophenyl, 2,3-difluorophenyl, 2,4-difluorophenyl, 2,5-difluorophenyl, 2,6-difluorophenyl, 2-fluoro-5-chlorophenyl, 4-fluoro-3-chlorophenyl, 4-fluoro-3-trifluoromethylphenyl, 2-fluoro-4-methylphenyl, 3-fluoro-4-methyl-phenyl, 3-chlorophenyl, 4-chlorophenyl, 3,4-dichlorophenyl, 2,6-dichlorophenyl, 3-chloro-4-methylphenyl or 4-methylphenyl; $R_1$ is methyl; $R_4$ is methyl and $R_5$ is benzyl.

54. The method of claim 53 wherein $R_2$ is hydrogen.

55. The method of claim 54 wherein R is 2,5-difluorophenyl.

56. The method of claim 54 wherein R is 2-fluoro-4-methylphenyl.

57. The method of claim 45 wherein R is 2-fluorophenyl, 2,6-difluorophenyl, 2-fluoro-3-chlorophenyl, 2-fluoro-4-methylphenyl, 3-fluoro-4-methylphenyl, 4-fluoro-3-trifluoromethylphenyl, 2-fluoro-4-bromophenyl, 2,5-difluoro-4-methylphenyl, 3-chlorophenyl, 3-chloro-4-methylphenyl, 4-methylphenyl, 3-iodophenyl or 4-bromophenyl; $R_1$ is methyl; $R_4$ is methyl and $R_5$ is phenethyl.

58. The method of claim 57 wherein $R_2$ is hydrogen.

59. The method of claim 58 wherein R is 2,5-difluorophenyl.

60. The method of claim 58 wherein R is 2-fluoro-4-methylphenyl.

61. The method of claim 58 wherein R is 2,5-difluoro-4-methylphenyl.

62. The method of claim 45 wherein R is phenyl 2-fluorophenyl, 4-fluorophenyl, 2-fluoro-4-methylphenyl or 4-chlorophenyl; $R_1$ is methyl; $R_4$ is ethyl and $R_5$ is phenyl.

63. The method of claim 45 wherein R is 2-fluorophenyl, $R_1$ is methyl; $R_4$ is isopropyl and $R_5$ is phenyl or phenalkyl.

64. The method of claim 45 wherein $R_2$ is hydrogen, $R_4$ is methyl; $R_5$ is phenyl or phenalkyl and V is sulfur.

65. The method of claim 41 wherein R is halophenyl; $R_2$ is alkyl; $R_4$ is $C_1-C_4$ lower alkyl and $R_5$ is phenyl or phenalkyl.

66. the method of claim 65 wherein R is 2-fluorophenyl; $R_1$ is methyl; $R_2$ is methyl; $R_4$ is methyl and $R_5$ is phenyl or benzyl.

67. The method of claim 65 wherein R is phenyl or halophenyl; $R_1$ is methyl; $R_2$ is hydrogen and $R_4$ and $R_5$ are independently $C_1-C_4$ alkyl, cycloalkyl, pyridyl, pyridylalkyl, phenalkyl, naphthyl, phenyl or halophenyl.

68. The method of claim 67 wherein R is halophenyl; $R_4$ is $C_1-C_4$ alkyl and $R_5$ is benzyl.

69. The method of claim 68 wherein R is halophenyl; $R_4$ is benzyl and $R_5$ is benzyl.

70. The method of claim 41 wherein R is phenyl or halophenyl; $R_1$ is $C_1-C_3$ alkyl; $R_2$ is hydrogen or methyl; $R_4$ and $R_5$ taken together with nitrogen form hexamethyleneimine, piperidine, phenylpiperidine, benzylpiperidine, indoline, or perhydroindole and V is oxygen.

71. The method of claim 41 wherein R is phenyl substituted with halo or alkyl, $R_1$ is ethyl; $R_2$ is hydrogen; $R_4$ is methyl; $R_5$ is phenyl and V is oxygen.

72. The method of claim 45 wherein R is phenyl, 4-chlorophenyl, 3-chloro-4-fluorophenyl, 3-chloro-4-methylphenyl, 3-methylphenyl, 3-methoxyphenyl, 4-methylphenyl, 4-methoxyphenyl, 3-methanesulfonylphenyl, 2-fluorophenyl, 3-fluorophenyl, 4-fluorophenyl, 2,3-difluorophenyl, 2,4-difluorophenyl, 2,5-difluorophenyl, 2-fluoro-4-chlorophenyl, 2-fluoro-4-bromophenyl, 3-fluoro-4-methylphenyl, 2-trifluoromethylphenyl, 3-trifluoromethylphenyl, 4-trifluoromethylphenyl or 3-trifluoromethyl-4-fluorophenyl; $R_1$ is methyl; $R_2$ is hydrogen; $R_4$ is methyl; $R_5$ is phenyl and V is oxygen.

73. The method of claim 41 wherein R is phenyl, 4-methylphenyl, 4-methoxyphenyl, 4-bromophenyl, 3-iodophenyl, 3-chlorophenyl, 4-chlorophenyl, 3,4-dichlorophenyl, 3,5-dichlorophenyl, 3-chloro-4-methylphenyl, 3-chloro-4-fluorophenyl, 2-fluorophenyl, 3-fluorophenyl, 2,3-difluorophenyl, 2,4-difluorophenyl, 2,5-difluorophenyl, 2,6-difluorophenyl, 2-fluoro-4-bromophenyl, 2-fluoro-3-chlorophenyl, 2-fluoro-4-chlorophenyl, 2-fluoro-5-chlorophenyl, 2-fluoro-4-chloro-5-methoxyphenyl, 2,5-difluoro-4-methylphenyl, 2-fluoro-4-methylphenyl, 3-fluoro-4-methylphenyl, 2-fluoro-4-methoxyphenyl, 2-fluoro-5-trifluoromethylphenyl, 2-trifluoromethylphenyl, 3-trifluoromethylphenyl, 4-trifluoromethylphenyl, or 3-trifluoromethyl-4-fluorophenyl; $R_1$ is methyl; $R_2$ is hydrogen; $R_4$ is hydrogen, methyl, ethyl, isopropyl, or butyl; $R_5$ is benzyl, 2-chlorobenzyl, 3-chlorobenzyl, 4-chlorobenzyl, phenethyl, or phenpropyl and V is oxygen.

74. The method of claim 45 wherein R is phenyl or halophenyl; $R_1$ is $C_1-C_3$ lower alkyl; $R_2$ is hydrogen; $R_4$ is methyl; R₅ is 2-pyridyl or 2-pyridylalkyl and V is oxygen.

75. The method of claim 74 wherein R₁ is methyl and R₅ is 2-pyridylethyl.

76. The method of claim 75 wherein R is 2-fluoro-4-methylphenyl.

77. The method of claim 41 wherein R is phenyl or halophenyl; R₁ is C₁-C₃ lower alkyl; R₂ is hydrogen; R₄ is C₁-C₄ alkyl; R₅ is C₃-C₆ cycloalkyl or C₃-C₆ alkylcycloalkyl and V is oxygen.

78. The method of claim 77 wherein R₅ is cyclohexyl.

79. The method of claim 77 wherein R is phenyl, 2-fluorophenyl, 2,5-difluorophenyl, 3-chlorophenyl or 3,4-dichlorophenyl; R₁ is methyl and R₄ is methyl or ethyl.

80. The method of claim 77 wherein R is halophenyl and R₅ is cyclopropylmethyl.

81. An herbicidal composition comprising:
(a) an herbicidally effective amount of a compound having the formula

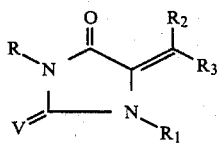

wherein R is C₁-C₆ alkyl, phenyl, phenyl substituted with one or more C₁-C₄ alkyl, C₁-C₄ alkylsulfonyl, C₁-C₄ alkoxy, halo, or C₁-C₄ haloalkyl;
R₁ is hydrogen, C₁-C₃ alkyl, phenyl or phenyl substituted with halo or C₁-C₆ alkyl;
R₂ is hydrogen or C₁-C₃ alkyl;
R₃ is

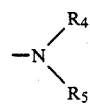

wherein R₄ and R₅ are independently hydrogen, C₁-C₆ alkyl, phenyl, halophenyl, phenalkyl, alkylphenalkyl, halophenalkyl, cycloalkyl, cycloalkylmethyl, naphthyl, pyridyl, pyridylalkyl, or R₄ and R₅ taken together with nitrogen form hexamethyleneimine, piperidine, phenylpiperidine, benzylpiperidine, indoline, or perhydroindoline; and
V is sulfur or oxygen; provided that when R is C₁-C₆ alkyl, R₁ is phenyl or phenyl substituted with one or more halo or C₁-C₆ alkyl and R₄ is alkyl or hydrogen and when R is phenyl or phenyl substituted with one or more C₁-C₄ alkyl, C₁-C₄ alkoxy, halo or C₁-C₄ haloalkyl and R₄ is alkyl or hydrogen, then R₅ is other than alkyl or hydrogen; and provided that when R₁ is methyl and R₃ is

wherein R₄ is methyl and R₅ is phenyl, then R is other than 2-chlorophenyl or 2-methoxyphenyl; and when R₁ is hydrogen or ethyl and R₃ is

wherein R₄ is methyl and R₅ is phenyl, then R is other than 3,4-dichlorophenyl; and
(b) an herbicidally suitable inert diluent or carrier.

82. An herbicidal composition according to claim 81 wherein R is methyl; R₁ is phenyl substituted with halo, alkyl or combinations thereof; R₂ is hydrogen; R₃ is a group having the formula

wherein R₄ is methyl; R₅ is phenalkyl or phenyl and V is oxygen.

83. An herbicidal composition according to claim 82 wherein R₁ is halophenyl.

84. An herbicidal composition according to claim 83 wherein R₁ is 2-fluorophenyl, 2,5-difluorophenyl or 2-fluoro-4-methylphenyl.

85. An herbicidal composition according to claim 84 wherein R₁ is halophenyl.

86. An herbicidal composition according to claim 85 wherein R is 2-fluorophenyl or 2,5-difluorophenyl.

87. An herbicidal composition according to claim 81 wherein R is phenyl, phenyl substituted with halo, alkyl, haloalkyl or combinations thereof, R₁ is alkyl; R₂ is hydrogen or methyl, R₃ is a group having the formula

−N(R₄)(R₅)

wherein R₄ and R₅ are independently hydrogen, alkyl, phenyl, halophenyl, benzyl, phenalkyl, pyridyl or pyridylalkyl and V is oxygen provided that when R₄ is alkyl, then R₅ is other than alkyl.

88. An herbicidal composition according to claim 87 wherein R is phenyl, 2-fluorophenyl, 3-fluorophenyl, 4-fluorophenyl, 2,4-difluorophenyl, 2,5-difluorophenyl, 2-fluoro-4-bromophenyl, 4-fluoro-3-chlorophenyl, 2-fluoro-4-chlorophenyl, 2-fluoro-4-methylphenyl, 2-chlorophenyl, 3-chlorophenyl, 4-chlorophenyl, 3,4-dichlorophenyl, 3-chloro-4-methylphenyl or 4-methylphenyl; R₁ is methyl; R₄ is methyl and R₅ is phenyl.

89. An herbicidal composition according to claim 88 wherein R₂ is hydrogen.

90. An herbicidal composition according to claim 89 wherein R is 2,5-difluorophenyl.

91. An herbicidal composition according to claim 89 wherein R is 2-fluoro-4-methylphenyl.

92. An herbicidal composition according to claim 87 wherein R is phenyl, halophenyl or haloalkylphenyl, R₁ is methyl, R₂ is hydrogen, R₄ is hydrogen or methyl and R₅ is halophenyl.

93. An herbicidal composition according to claim 92 wherein R is 4-chlorophenyl, 3-trifluoromethylphenyl or 2,5-difluorophenyl; R₄ is methyl and R5 is halophenyl.

94. An herbicidal composition according to claim 92 wherein R is phenyl or 3,4-dichlorophenyl; $R_4$ is hydrogen and $R_5$ is halophenyl.

95. An herbicidal composition according to claim 87 wherein R is phenyl, 2-fluorophenyl, 3-fluorophenyl, 2,3-difluorophenyl, 2,4-difluorophenyl, 2,5-difluorophenyl, 2,6-difluorophenyl, 2-fluoro-5-chlorophenyl, 4-fluoro-3-chlorophenyl, 4-fluoro-3-trifluoromethylphenyl, 2-fluoro-4-methylphenyl, 3-fluoro-4-methylphenyl, 3-chlorophenyl, 4-chlorophenyl, 3,4-dichlorophenyl, 2,6-dichlorophenyl, 3-chloro-4-methylphenyl or 4-methylphenyl; $R_1$ is methyl; $R_4$ is methyl and $R_5$ is benzyl.

96. An herbicidal composition according to claim 95 wherein $R_2$ is hydrogen.

97. An herbicidal composition according to claim 96 wherein R is 2,5-difluorophenyl.

98. An herbicidal composition according to claim 96 wherein R is 2-fluoro-4-methylphenyl.

99. An herbicidal composition according to claim 87 wherein R is 2-fluorophenyl, 2,6-difluorophenyl, 2-fluoro-3-chlorophenyl, 2-fluoro-4-methylphenyl, 3-fluoro-4-methylphenyl, 4-fluoro-3-trifluoromethylphenyl, 2-fluoro-4-bromophenyl, 2,5-difluoro-4-methylphenyl, 3-chlorophenyl, 3-chloro-4-methylphenyl, 4-methylphenyl, 3-iodophenyl or 4-bromophenyl; $R_1$ is methyl; $R_4$ is methyl and $R_5$ is phenethyl.

100. An herbicidal composition according to claim 99 wherein $R_2$ is hydrogen.

101. An herbicidal composition according to claim 100 wherein R is 2,5-difluorophenyl.

102. An herbicidal composition according to claim 100 wherein R is 2-fluoro-4-methylphenyl.

103. An herbicidal composition according to claim 100 wwherein R is 2,5-difluoro-4-methylphenyl.

104. An herbicidal composition according to claim 87 wherein R is phenyl, 2-fluorophenyl, 4-fluorophenyl, 2-fluoro-4-methylphenyl or 4-chlorophenyl; $R_1$ is methyl; $R_4$ is ethyl and $R_5$ is phenyl.

105. An herbicidal composition according to claim 87 wherein R is 2-fluorophenyl; $R_1$ is methyl; $R_4$ is isopropyl and $R_5$ is phenalkyl.

106. An herbicidal composition according to claim 87 wherein $R_2$ is hydrogen, $R_4$ is methyl; $R_5$ is phenyl or phenalkyl and V is sulfur.

107. An herbicidal composition according to claim 81 wherein R is halophenyl; $R_2$ is alkyl; $R_4$ is $C_1$-$C_4$ lower alkyl and $R_5$ is phenyl or phenalkyl.

108. An herbicidal composition according to claim 107 wherein R is 2-fluorophenyl; $R_1$ is methyl; $R_2$ is methyl; $R_4$ is methyl and $R_5$ is phenyl or benzyl.

109. An herbicidal composition according to claim 108 wherein R is phenyl or halophenyl; $R_1$ is methyl; $R_2$ is hydrogen and $R_4$ and $R_5$ are independently $C_1$-$C_4$ alkyl, cycloalkyl, pyridyl, pyridylalkyl, phenalkyl, naphthyl, phenyl or halophenyl.

110. An herbicidal composition according to claim 109 wherein R is halophenyl; $R_4$ is $C_1$-$C_4$ alkyl and $R_5$ is benzyl.

111. An herbicidal composition according to claim 110 wherein R is halophenyl; $R_4$ is benzyl and $R_5$ is benzyl.

112. An herbicidal composition according to claim 81 wherein R is phenyl or halophenyl; $R_1$ is $C_1$-$C_3$ alkyl; $R_2$ is hydrogen or methyl; $R_4$ and $R_5$ taken together with nitrogen form hexamethyleneimine, piperidine, phenylpiperidine, benzylpiperadine, indoline, or perhydroindole and V is oxygen.

113. An herbicidal composition according to claim 81 wherein R is phenyl substituted with halo or alkyl, $R_1$ is ethyl; $R_2$ is hydrogen; $R_4$ is methyl; $R_5$ is phenyl and V is oxygen.

114. An herbicidal composition according to claim 81 wherein R is phenyl, 4-chlorophenyl, 3-chloro-4-fluorophenyl, 3-chloro-4-methylphenyl, 3-methylphenyl, 3-methoxyphenyl, 4-methylphenyl, 4-methoxyphenyl, 3-methanesulfonylphenyl, 2-fluorophenyl, 3-fluorophenyl, 4-fluorophenyl, 2,3-difluorophenyl, 2,4-difluorophenyl, 2,5-difluorophenyl, 2-fluoro-4-chlorophenyl, 2-fluoro-4-bromophenyl, 3-fluoro-4-methylphenyl, 2-trifluoromethylphenyl, 3-trifluoromethylphenyl, 4-trifluoromethylphenyl or 3-trifluoromethyl-4-fluorophenyl; $R_1$ is methyl; $R_2$ is hydrogen; $R_4$ is methyl; $R_5$ is phenyl and V is oxygen.

115. An herbicidal composition according to claim 81 wherein R is phenyl, 4-methylphenyl, 4-methoxyphenyl, 4-bromophenyl, 3-iodophenyl, 3-chlorophenyl, 4-chlorophenyl, 3,4-dichlorophenyl, 3,5-dichlorophenyl, 3-chloro-4-methylphenyl, 3-chloro-4-fluorophenyl, 2-fluorophenyl, 3-fluorophenyl, 2,3-difluorophenyl, 2,4-difluorophenyl, 2,5-difluorophenyl, 2,6-difluorophenyl, 2-fluoro-4-bromophenyl, 2-fluoro-3-chlorophenyl, 2-fluoro-4chlorophenyl, 2-fluoro-5-chlorophenyl, 2-fluoro-4-chloro-5-methoxyphenyl, 2,5-difluoro-4-methylphenyl, 2-fluoro-4-methylphenyl, 3-fluoro-4-methylphenyl, 2-fluoro-4-methoxyphenyl, 2-fluoro-5-trifluoromethylphenyl, 2-trifluoromethylphenyl, 3-trifluoromethylphenyl, 4-trifluoromethylphenyl, or 3-trifluoromethyl-4-fluorophenyl; $R_1$ is methyl; $R_2$ is hydrogen; $R_4$ is hydrogen, methyl, ethyl, isopropyl, or butyl; $R_5$ is benzyl, 2-chlorobenzyl, 3-chlorobenzyl, 4-chlorobenzyl, phenethyl, or phenpropyl and V is oxygen.

116. An herbicidal composition according to claim 87 wherein R is phenyl or halophenyl; $R_1$ is $C_1$-$C_3$ lower alkyl; $R_2$ is hydrogen; $R_4$ is methyl; $R_5$ is 2-pyridyl or 2-pyridylalkyl and V is oxygen.

117. An herbicidal composition according to claim 116 wherein $R_1$ is methyl and $R_5$ is 2-pyridylethyl.

118. An herbicidal composition according to claim 117 wherein R is 2-fluoro-4-methylphenyl.

119. An herbicidal composition according to claim 81 wherein R is phenyl or halophenyl; $R_1$ is $C_1$-$C_3$ lower alkyl; $R_2$ is hydrogen; $R_4$ is $C_1$-$C_4$ alkyl; $R_5$ is $C_3$-$C_6$ cycloalkyl or $C_3$-$C_6$ alkylcycloalkyl and V is oxygen.

120. An herbicidal composition according to claim 119 wherein $R_5$ is cyclohexyl.

121. An herbicidal composition according to claim 119 wherein R is phenyl, 2-fluorophenyl, 2,5-difluorophenyl, 3-chlorophenyl or 3,4-dichlorophenyl; $R_1$ is methyl and $R_4$ is methyl or ethyl.

122. An herbicidal composition according to claim 119 wherein R is halophenyl and $R_5$ is cyclopropylmethyl.

* * * * *